United States Patent [19]

Barra et al.

[11] Patent Number: 5,696,242

[45] Date of Patent: Dec. 9, 1997

[54] POLYAZO DYES CONTAINING THE RADICAL OF A BIS-COUPLING COMPONENT, AND PROCESS FOR THEIR PRODUCTION

[75] Inventors: Jordi Berenguer Barra; Jose Rocas Sorolla, both of Barcelona, Spain

[73] Assignee: Clariant Finance (BVI) Limited, Tortola, Virgin Islands (Br.)

[21] Appl. No.: 510,206

[22] Filed: Aug. 2, 1995

[30] Foreign Application Priority Data

Aug. 4, 1994 [GB] United Kingdom ............ 9415786

[51] Int. Cl.$^6$ .............. C09B 31/30; C09B 33/18; C09B 29/036; C09B 35/50; C09B 67/22
[52] U.S. Cl. .............. 534/647; 534/573 M; 534/757
[58] Field of Search .............. 534/647, 573 M, 534/757

[56] References Cited

U.S. PATENT DOCUMENTS

| | | | |
|---|---|---|---|
| 3,134,761 | 5/1964 | Ackermann | 534/795 |
| 3,197,455 | 7/1965 | Jung | 534/758 |
| 3,206,453 | 9/1965 | Merian et al. | 534/647 |
| 3,657,218 | 4/1972 | Gnad et al. | 534/647 X |
| 4,171,975 | 10/1979 | Kato et al. | 430/253 |
| 4,340,536 | 7/1982 | Beffa | 534/695 |
| 4,563,193 | 1/1986 | Beffa | 8/685 |
| 4,652,631 | 3/1987 | Beffa et al. | 534/645 |
| 5,077,396 | 12/1991 | Moser et al. | 534/606 |
| 5,334,709 | 8/1994 | Dannheim et al. | 534/618 |

FOREIGN PATENT DOCUMENTS

| | | |
|---|---|---|
| 1 329 211 | 4/1963 | France . |
| 1056758 | 5/1959 | Germany . |
| 1072338 | 12/1959 | Germany ............ 534/647 |
| 1151080 | 7/1963 | Germany . |
| 3512078 | 10/1985 | Germany . |
| 0371200 | 9/1963 | Switzerland ............ 534/647 |
| 393592 | 12/1965 | Switzerland . |
| 868 594 | 5/1961 | United Kingdom . |

OTHER PUBLICATIONS

Search Report, GB 9415786.4, dated 29 Sep. 1994.

*Primary Examiner*—Floyd D. Higel
*Attorney, Agent, or Firm*—Hesna J. Pfeiffer

[57] ABSTRACT

The invention provides a compound of formula

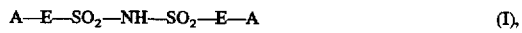

wherein
each —E—, independently, signifies a bivalent aromatic radical,
each —A, independently, signifies a heterocyclic group of formula

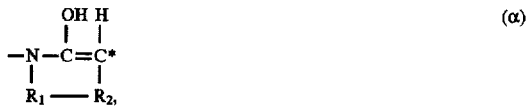

and
the group —R$_1$—R$_2$— signifies a 2- or 3-membered bridging chain to form, together with the group

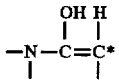

to which it is bound, a 5- or 6-membered heterocycle, with the proviso that the carbon indicated by the asterisk * is capable of being coupled with a diazonium compound, or a mixture of compounds of formula (I), and the use thereof as (bis)coupling components for the production of azodyes and metal complexes, which are useful as dyes, especially for the dyeing of leather.

14 Claims, No Drawings

POLYAZO DYES CONTAINING THE RADICAL OF A BIS-COUPLING COMPONENT, AND PROCESS FOR THEIR PRODUCTION

It has been found that particular bis-(arylsulphonyl)-amines that are terminated by a defined nitrogen-containing heterocyclic radical that contains a methylene group which is activated by a neighbouring carbonyl group, so that the activated positions are capable of coupling reactions with diazotized amines, are eminently suitable as coupling components, in particular bis-coupling components, for the production of azo dyes, in particular polyazo dyes. In this way there may, in particular, be obtained polyazo dyes and also metal complexes of outstanding colouristic properties and that are suitable for the dyeing of various substrates, especially leather, in various shades of notable fastness properties.

The invention relates to these below-defined compounds, their production and their use as coupling components for the production of azo dyes and their derivatives and also to the corresponding azo dyes and their metal complexes, their production and their use.

The invention, thus, provides a compound of formula $$A\!-\!E\!-\!SO_2\!-\!NH\!-\!SO_2\!-\!E\!-\!A \quad (I),$$

wherein each —E—, independently, signifies a bivalent aromatic radical, each —A, independently, signifies a heterocyclic group of formula

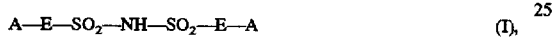

and the group —R$_1$—R$_2$— signifies a 2- or 3-membered bridging chain to form, together with the group

to which it is bound, a 5- or 6-membered heterocycle, with the proviso that the carbon indicated by the asterisk * is capable of being coupled with a diazonium compound, or a mixture of compounds of formula (I).

Preferably —E— is an aromatic carbocyclic radical that may contain one or more, preferably one or two, aromatic rings, which may be further substituted. The substituents, if any, and their positions at these aromatic rings in —E— are suitably chosen so that any coupling of a diazo compound takes place, at least preferentially, at the indicated carbon atom of —A. Advantageously —E— is a phenylene radical that may be further substituted (e.g. with $C_{1-4}$-alkyl, $C_{1-4}$-alkoxy or/and chlorine) or a naphthylene radical which is preferably further unsubstituted. If —E— signifies naphthylene, the —SO$_2$-group is preferably in its 1-position and the radical —A is preferably in the position 3 or 4, more preferably 4. If —E— is a substituted phenylene radical, it is preferably monosubstituted; the substituent is preferably a methyl group. More preferably any phenylene as —E— is preferably unsubstituted. The radical —A is preferably in position meta or para, more preferably para to the group —SO$_2$—.

The group —R$_1$—R$_2$—, which signifies a 2- or 3-membered bridging chain to form as —A a 5- or 6-membered heterocycle, may optionally contain a heteroatom, in particular a further nitrogen atom, and/or one or more double bonds and/or may optionally be substituted. The group of formula (α) signifies preferably a heterocycle of the pyridone or pyrazolone series.

Preferred radicals of formula (α) of the pyrazolone series correspond to the following formula

wherein R$_3$ signifies $C_{1-4}$-alkyl or carboxy.

Among the $C_{1-4}$-alkyl radicals in formula (α1) in the significance of R$_3$ the lower molecular ones are preferred, especially methyl.

Preferred radicals of formula (α) of the pyridone series correspond to the following formula

wherein

R$_4$ signifies hydrogen, nitril, carbamoyl, acetyl, carboxy, sulpho, pyridinio or 2-methyl-pyridinio and R$_5$ signifies hydrogen, methyl, hydroxy, phenyl, carbamoyl, carboxy or sulphomethyl.

In the significance of R$_4$ are preferred hydrogen, sulpho or one of the nitrogen-containing substituents, especially nitril.

R$_5$ preferably has a significance other than hydrogen; more preferably R$_5$ signifies methyl.

Most preferably —A is a radical of the pyrazolone series, in particular as defined by formula (α1).

Preferred compounds of formula (I) are those of the formula

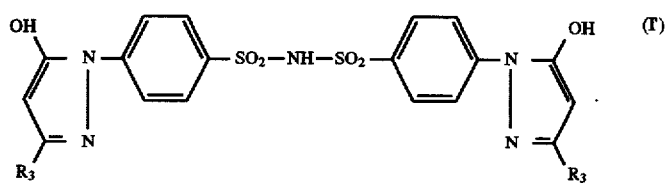

Particularly preferred is the compound of formula (I') in which R$_3$ signifies methyl.

The compounds of formula (I) may be synthetised by acylation and cyclization reactions conventional per se of suitable amino-group-containing compounds. In particular the process for the production of the compounds of formula (I) or mixtures of compounds of formula (I) is characterized in that a compound of formula

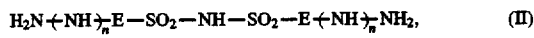

wherein n signifies 0 or 1,
or a mixture of compounds of formula (II) is reacted with suitable dicarbonyl compound, e.g. a functional derivative of an acylacetic acid or a diketene, and, if required, with further reactants as required to convert each group —$NH_2$ or —NH—$NH_2$ to the respective radical —A of formula (α).

The acylation may e.g. be carried out with the corresponding acyl halide (preferably chloride or bromide, more preferably chloride) under dehydrohalogenating conditions or with a diketene. This reaction is suitably carried out on compounds of formula (II) in which n signifies 0. For the production of the pyrazolone groups of formula (α1) the starting compound of formula (II) is suitably a compound or mixture in which n signifies 1 and the acylation with the respective acylacetic acid halide, e.g. bromide or chloride, or with the diketene is followed or accompanied by the cyclization reaction under cleavage of water. Alternatively the reaction may be carried out with acylacetic acid amide in aqueous, strongly acidic medium, with heating.

The starting bishydrazino derivative of formula (II) in which n =1 may be produced by diazotizing a starting bis-amino compound of formula (II) in which n =0 and reducing the bisdiazo compound with a conventional reducing agent, preferably with sodium bisulphite or/and sodium sulphite or with iron turnings in the presence of a weak acid e.g. acetic acid.

The synthesis of disulphanilamide from N-acetyl-sulphanil chloride of formula

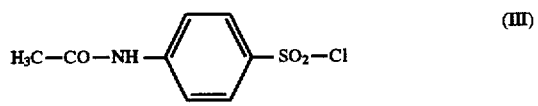

and ammonia, in the presence of NaOH at pH 10-11, is described by M. L. CROSSLEY et al. in "Journal of the American Chemical Society", 60 (1938), at pages 2222-2224. It may also be produced by reaction of 4-acetylaminobenzenesulphonamide with N-acetyl-sulphanil chloride of formula (III) under alkaline conditions, preferably at pH 10-11 with NaOH and at temperatures between 50° and 80° C., as suitable for dehydrohalogenation and then hydrolysis of the acetylamino group. The analogous or homologous compounds, in which E has another of the above stated significances, may be produced in an analogous way (l.c. pages 2217–2224). Thus, dimetanil-amide and diorthanilamide are synthetized from o- or m-nitrobenzenesulphonyl chloride and ammonia, at pH 8-10 with NaOH, and subsequent reduction of the nitro groups to amino groups with sodium sulphide or by the Béchamps reduction (with Fe and a weak acid, e.g. acetic acid). Dinaphthionylamide may be synthetized, analogously to disulphanil amide, e.g. from N-acetylnaphthionyl chloride and ammonia at pH 10-11 with NaOH.

The production of compounds of formula (I) in which —A signifies a pyridone ring of formula (α2) may also take place in a manner known per se, by reacting a bis-amino compound of formula (II) in which n signifies 0, e.g. with an acylacetic acid ester and another suitable reactant, as required for ring closure, e.g. analogously to the known GUABESCHI/THORPE reaction or by another suitable method known per se, or by reaction of an open-chain acyl-acetylamino precursor compound with a suitable functional derivative of an acid of formula $R_4$—$CH_2$—COOH, e.g. its methyl ester, under cyclizing reaction conditions.

The compounds of formula (I), that contain as —A the radicals of formula (α) and which may be represented by the formula

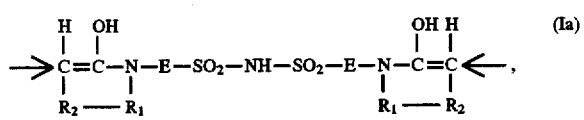

contain two positions (indicated in the above formula by the two arrows) capable of coupling reactions with diazo compounds and are particularly useful as coupling components (BK) for the production of azo dyes, especially of polyazo dyes.

The invention, thus, further provides a process for the production of an azo dye or mixture of azo dyes by diazotization and coupling reactions and optionally further reactions, wherein a compound of formula (I) or mixture thereof is employed as a coupling component (BK).

For the production of the azo dyes, in particular polyazo dyes, there may be employed one or more diazo compounds of correspondingly one or more diazo components (DK).

The invention, thus, provides also an azo dye (AZ) characterized by comprising a radical of a coupling component (BK) as a constituent component of the azo dye molecule, or a mixture of azo dyes (AZ).

In particular the invention provides also an azo dye (AZ) or mixture as defined above, which is a polyazo dye ($AZ_1$), characterized by comprising a radical of a bis-coupling component (BK) as a constituent component of the polyazo dye ($AZ_1$), or a mixture of polyazo dyes ($AZ_1$).

More particularly the azo dyes (AZ) of the invention, or more specifically the polyazo dyes ($AZ_1$), as defined above, are preferably at least disazo dyes, which may be represented by the formula

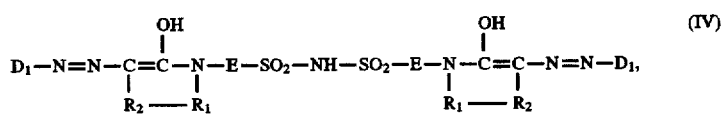

wherein each —$D_1$, independently, is the radical of a diazo component (DK), and may also be mixtures of azo dyes of formula (IV).

—$D_1$ may signify the radical of any diazo component as suitable for the production of azo dyes, or a modified derivative thereof. In particular each —$D_1$ may signify the radical of a diazo component that may optionally contain one or more, e.g. one or two, further azo groups, particularly as deriving from the diazotization of an amine of formula $D_1'$—$NH_2$. Where —$D_1$ contains one or more azo groups, these may e.g. derive from previous diazotization and coupling reactions and optionally other suitable modification reactions (e.g. hydrolysis of an acylated aminogroup or reduction of a nitrogroup to give a primary aminogroup) to give—as $D_1'$—$NH_2$ —an azogroup-containing compound that contains a diazotizable primary aminogroup, preferably of the formula $$D_2 + N=N-X \}_x NH_2, \quad (V)$$

wherein

—X— signifies the bivalent radical of a middle component (MK), x is 1 or 2 and

—$D_2$ signifies the radical of a diazo component (DK') of formula D—$NH_2$ that preferably does not contain an azogroup.

—X— may be the radical of any middle component (MK) in particular of formula H—X— $NH_2$—as a middle component there being understood a compound capable of a coupling reaction with a diazocompound and also of being itself (before or after said coupling reaction) diazotized and coupled to a further coupling component-and contains e.g. 1 to 4, preferably 2 or 3, aromatic rings (a naphthalene nucleus being calculated as two aromatic rings). —X— may e.g. contain one or two benzenic nuclei or/and a naphthalenic nucleus and optionally an at least partially aromatic heterocyclic ring. In particular —X— may signify a grouping —G—Y—$E_1$— deriving in particular from an (MK) of formula H—G—Y—$E_1$—$NH_2$, so that in this case formula (V) corresponds to the formula $$D_2 + N=N-G-Y-E_1 \}_x NH_2, \quad (Va)$$

wherein

—$E_1$— signifies a bivalent aromatic radical of the benzene or naphthalene series, —G— signifies a bivalent aromatic radical of the hydroxybenzene series, of the 5-pyrazolone or -aminopyrazole series or of the amino- and/or hydroxypyrimidine series and —Y— signifies a heteroatomic bridge or, if —G— is of the 5-pyrazolone or -aminopyrazole series, the direct bond linked to the 1-position of the pyrazole resp. pyrazolone ring.

If x signifies 2, the two radicals —X— may have the same significance or different significances, respectively the two middle components (MK) may be equal or different.

Optionally —$D_1$ may contain a metallizable substituent in ortho- to the azo group or may contain a metallizable azo group, i.e. an azo-group-containing grouping that contains, in addition to this azo-group, two further substituents enabling metallization, i.e. such a substituent in an ortho-position to each of the two nitrogens of this azo group, e.g. —$NH_2$ or preferably —OH in ortho to the coupling position and —COOH or —OH in ortho- to the diazotized amino group.

Such metallizable compounds are in particular compounds of formula (V), or mixtures thereof, wherein —$D_2$signifies the radical of a diazocomponent (DK") of formula $$HZ_1-D_2'-NH_2,$$

in which —$Z_1H$ signifies —OR or —COOH and is in ortho-position to the diazotizable aminogroup and —$D_2'$— is the ortho-bivalent radical, or its modified derivative, and the adjacent —X— signifies $$-X'-Z_2H,$$

in which —$Z_2H$ signifies —OH or —$NH_2$ and is in ortho-position to $D_2$—N=N—, or, in the case of an (MK) containing a strongly acidic acylated aminogroup (e.g. an aromatically substituted sulphamoyl group) in meta-position to —$Z_2H$, $D_2$—N=N— may also be in para-position to —$Z_2H$ and ortho-position to this acylated aminogroup, whose —NH— group in this case is also capable of metal complex formation.

They may be represented by the following formula $$\begin{array}{c} D'_2-N=N-X'+N=N-X\}_y NH_2, \\ | \quad\quad\quad\quad | \\ Z_1H \quad\quad\quad\quad Z_2H \end{array} \quad (V')$$

in which y signifies 0 or 1, in particular by the formula $$\begin{array}{c} D'_2-N=N-G_1-Y-E_1+N=N-X\}_y NH_2, \\ | \quad\quad\quad\quad\quad\quad\quad\quad\quad | \\ Z_1H \quad\quad\quad\quad\quad\quad\quad\quad Z_2H \end{array} \quad (V'')$$

wherein —$G_1(Z_2H)$—corresponds to the significance of —G— above, in which —$Z_2H$ indicates the hydroxy- or primary amino-group of —G— and =$G_1$— represents the remaining portion of —G—.

According to a particular feature of the invention —N=N—X— signifies —N=N—G— —Y—$E_1$—.

Preferred polyazodyes ($AZ_x$) according to the invention are of formula

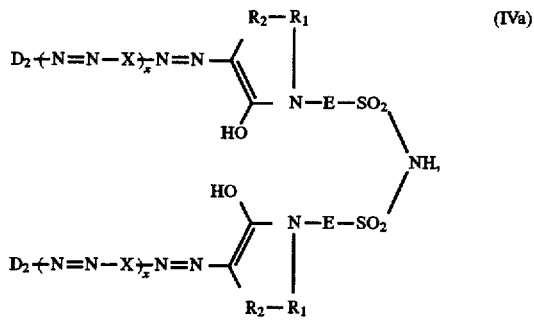

(IVa)

in which the two symbols —$D_2$ may have the same significance or different significances, the two indexes x may have the same significance or different significances and the two symbols —X— may have the same significance or different significances, and mixtures thereof.

Where all —X— signify each a grouping —G—Y—$E_1$— formula (IVa) corresponds to the formula

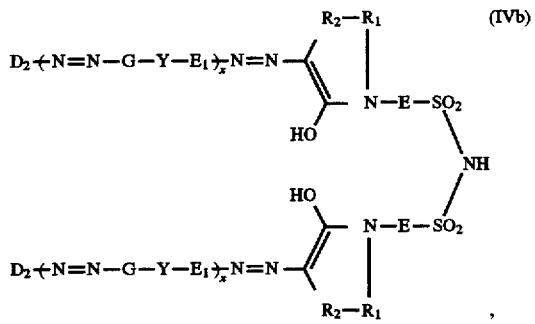 (IVb)

Particularly preferred polyazo dyes (AZ$_1$) according to the invention are polyazo dyes (AZ$_2$) of the formula

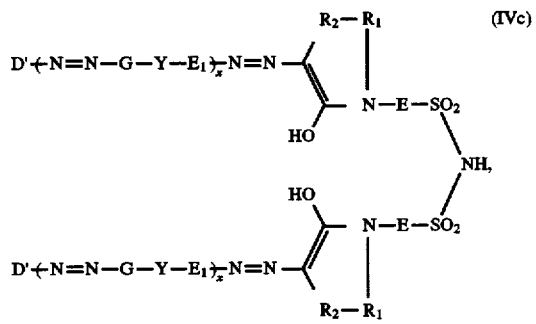 (IVc)

wherein each —D'—, independently, is the radical of a mono- or bicyclic diazocomponent of the benzene series or of a bicyclic diazocomponent of the naphthalene series, or mixtures of polyazo dyes (AZ$_2$).

Preferably —E$_1$— is an aromatic carbocyclic radical that contains one or two aromatic rings, which may be further substituted. Advantageously —E$_1$— is —E$_1$'—, i.e. phenylene that may be further substituted (e.g. with $C_{1-4}$-alkyl, $C_{1-4}$-alkoxy or/and chlorine) or naphthylene which is preferably further unsubstituted. If —E$_1$'— signifies naphthylene the bridge —Y— is preferably in its 1—position and the azo group is preferably in the position 3 or 4, more preferably 4

Where —Y— signifies a heteroatomic bridge this may be e.g. —NH—, —O—, —SO$_2$—, —CO—NH—, —NH—CO—NH—, an azo group or —SO$_2$—NH—. The significance of —Y— will advantageously be chosen depending on the nature of —G—. Most preferably —Y— (where it does not signify the direct bond) signifies a sulphonylamino bridge, in which the aminogroup is linked to —G—.

Preferably the polyazodyes of formula (IV), (IVa), (IVb) and (IVc) are tetra- to hexakisazodyes.

Where D$_1$—N=N— signifies a radical of the formula

 (β1)

or, preferably,

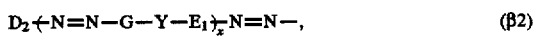 (β2)

each bridging group —X—N=N—, resp. —G—Y—E$_1$—N=N—, preferably derives from a middle component (MK) of the formula

H—G—Y—E$_1$—NH$_2$ (VI), which preferably is a compound of the formula

 (VIa)

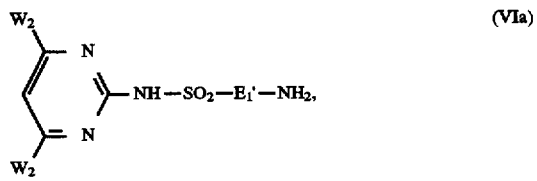 (VIb)

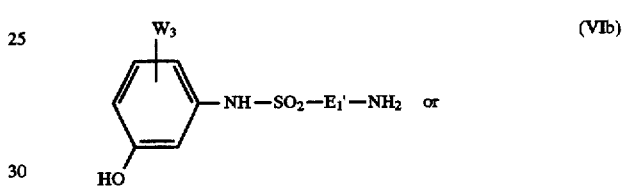

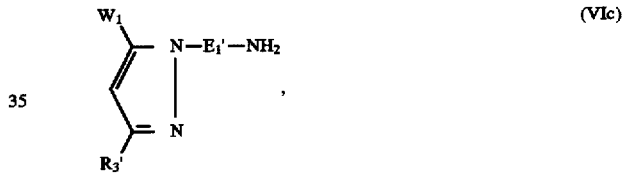 (VIc)

in which

W$_1$ signifies a primary amino group or hydroxy,

W$_2$ signifies a primary amino group or hydroxy,

W$_3$ signifies hydrogen, hydroxy, a primary amino group, $C_{1-4}$-alkyl or halogen and R$_3$', independently from R$_3$, has one of the significances of R$_3$.

—E$_1$'— is preferably phenylene-1,4

W$_3$ preferably signifies hydrogen.

Among the middle components of formulae (VIa), (VIb) and (VIc) those of formula (VIa) are preferred.

Especially preferred dyes of formula (Irc) are of formula

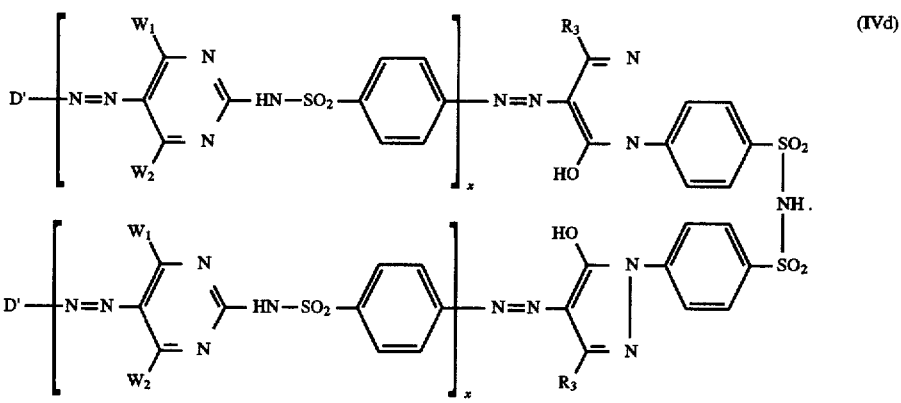
(IVd)

The compounds of formula (VI) are known or may be produced in a manner analogous to known methods. The compounds of formula (VIa) may be produced by reacting a guanide of formula

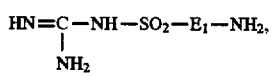 (VII)

in particular of formula

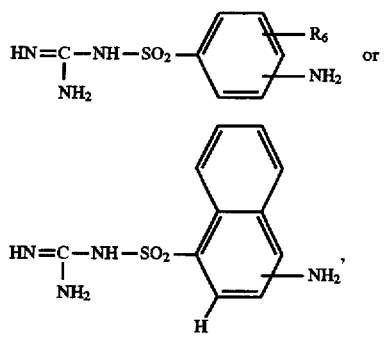

in which $R_6$ signifies hydrogen or methyl and the aromatically bound amino-group is optionally acylated with Ac, Ac being a protecting acyl group, e.g. benzoyl or $C_{1-3}$-alkyl-carbonyl,
with a compound of formula

Z'—CH$_2$—Z" (VIII), in which
Z' signifies —CN or —CO—($C_{1-2}$-alkyl) and
Z" signifies —CN or —CO—($C_{1-2}$-alkyl),
under cyclizing reaction conditions.

This reaction is carried out expediently in the presence of an akali metal alcoholate, preferably sodium methanolate, ethanolate or isopropanolate, optionally in the presence of alcohol (but suitably in the absence of water or other protogenic solvents that might react preferentially with the alkali metal alcoholate), with heating, preferably at temperatures ≧60° C., more preferably under reflux.

If desired, in the cyclization product a primary amino group linked to —$E_1$, in particular to a benzene or naphthalene ring, may be acylated in a manner conventional per se, preferably with Ac.

The compounds of formula (VII) may be produced in a manner conventional per se, in particular by amidation of guanidine with the respective sulphonic acid halide, in particular chloride or bromide, of formula Hal—SO$_2$—$E_1$—NHAc (IX), in particular

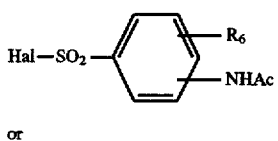 (IX')

or

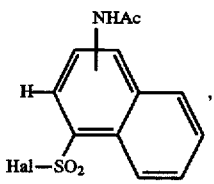 (IX"), in which

Hal signifies halogen, preferably Br or Cl, and Ac is as defined above, and, if desired, splitting off any group Ac by selective hydrolysis.

The compounds of formula (VIb) may be produced by selective acylation of a corresponding meta-aminophenol, analogously as described in the above M. L. CROSSLEY et al. publication.

Suitable amines D—NH$_2$ are, in particular, those of the following formulae

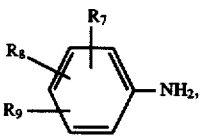 (a$_1$)

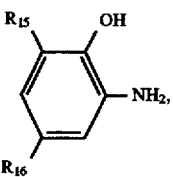 (a$_2$)

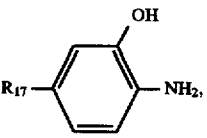 (a$_3$)

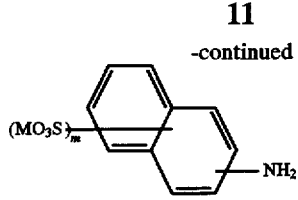

and

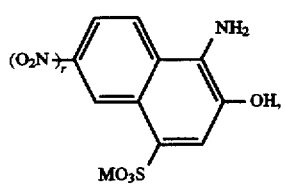

wherein $R_7$ signifies hydrogen, nitril, trifluoromethyl, nitro, —$SO_3M$, —$SO_2NR_{10}R_{11}$, —COOM or —$CONR_{10}R_{11}$, $R_8$ signifies hydrogen, nitro, —$SO_3M$, —$SO_2NR_{10}R_{11}$, trifluoromethyl, nitril, —COOM, —$CONR_{10}R_{11}$, $C_{1-4}$-alkyl, $C_{1-4}$-alkoxy, halogen or $C_{1-2}$-mercaptoalkyl, $R_9$ signifies hydrogen, $C_{1-4}$-alkyl, $C_{1-4}$-alkoxy, halogen, $C_{1-2}$—mercaptoalkyl, —NH—Ac', —NH—CO—O—CH$_3$ or a radical of formula

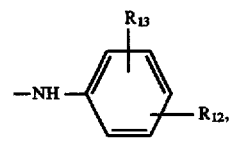

$R_{10}$ signifies hydrogen, $C_{1-4}$-alkyl, $C_{1-3}$-alkylene-R' or $C_{2-3}$-hydroxyalkyl, $R_{11}$ signifies hydrogen, $C_{1-4}$-alkyl, $C_{1-3}$-alkylene-R', $C_{2-3}$-hydroxyalkyl, benzyl or a radical of formula

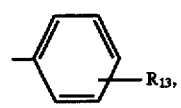

$R_{12}$ signifies hydrogen, nitro or —$SO_3M$, $R_{13}$ signifies hydrogen, methyl, chlorine, nitro, —COOM or —$SO_3M$, $R_{14}$ signifies nitril, carbamoyl or —COOM, $R_{15}$ signifies hydrogen, halogen, nitro, —$SO_3M$, —$SO_2NR_{10}R_{11}$, methylsulphonyl, $C_{1-4}$-alkyl or —NH—Ac', $R_{16}$ signifies hydrogen, halogen, nitro, —$SO_3M$, —$SO_2NR_{10}R_{11}$, methylsulphonyl, $C_{1-4}$-alkyl or —NH—Ac', $R_{17}$ signifies nitro, —$SO_3M$ or —$SO_2NR_{10}R_{11}$, m signifies 0 or 1 and r signifies 0 or 1.

Suitable middle components (MK) are in particular those of the following formulae

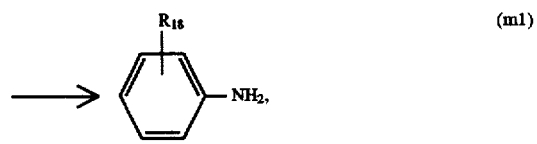

(m1)

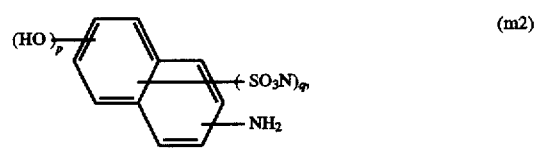

(m2)

and

(m3)

wherein $R_{18}$ signifies hydrogen, $C_{1-4}$-alkyl, $C_{1-4}$-alkoxy, hydroxy, —$NH_2$ or —NH—Ac', Ac' signifies an aliphatic acyl group, p signifies 0 or 1 and q signifies 0, 1 or 2.

Preferred diazocomponents (DK)—in particular amines $D_1'$—$NH_2$—correspond to the formulae

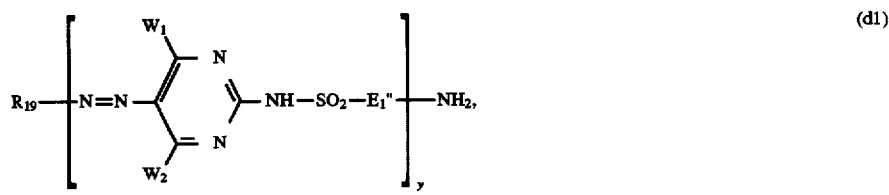

(d1)

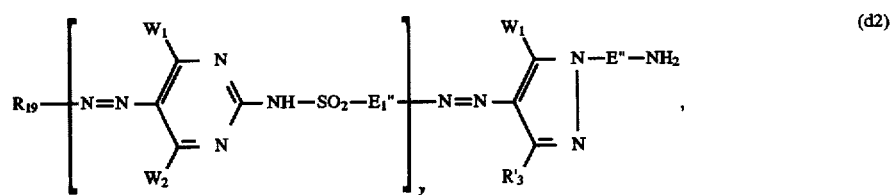

(d2)

and

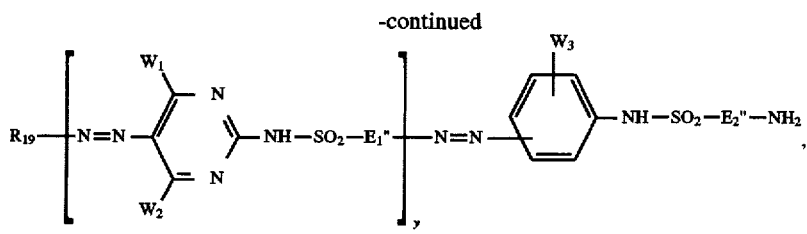

wherein $R_{19}$ signifies the radical of a diazocomponent deriving from the diazotization of an amine of formula ($a_1$), ($a_2$), ($a_3$), ($a_4$) or ($a_5$), and and —$E_1'$-signifies phenylene-1,3 or -1,4 or naphthylene-1, 4, preferred (DK) of formula (d3) being those of formula

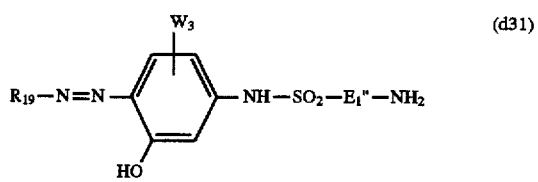

and

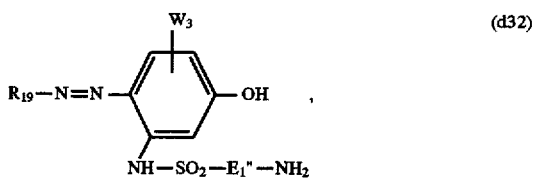

and preferred (DK) of formula (d1) corresponding to formula

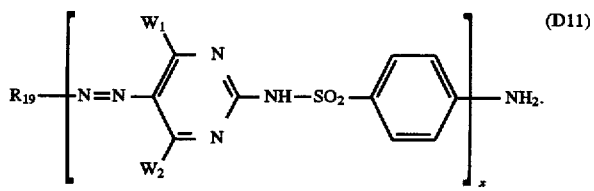

$R_7$ preferably signifies hydrogen or —COOM.

Of the alkyl and alkoxy groups with 1 to 4 carbon atoms, the lower molecular ones are preferred, in particular ethyl, methyl, ethoxy and methoxy. Halogen may in particular be fluorine, chlorine or bromine of which fluorine and, before all, chlorine are preferred.

Where in formula ($a_1$) $R_9$ signifies a radical of formula ($c_1$) this is preferably in para-position to the amino group, $R_7$ preferably signifies hydrogen, $R_8$ preferably signifies hydrogen or a sulpho group and, if $R_8$ signifies a sulpho group, this is preferably in meta-position to the azo group and $R_{12}$ and $R_{13}$ preferably signify both hydrogen or, if $R_8$ signifies hydrogen, $R_{10}$ signifies preferably a nitro group and $R_{11}$ signifies preferably a carboxy group or a sulpho group, the two substituents $R_{12}$ and $R_{13}$ being placed in the para-position to the imino group and in one of the two ortho-positions to the imino group.

Where the symbol $R_9$ does not signify a radical ($c_1$), $R_9$ preferably signifies hydrogen and $R_7$ preferably signifies hydrogen or —COOM. According to a preferred feature, in this case in formula ($a_1$) one or both of the positions ortho-to the primary amino group and, more preferably, also one or both of the positions meta to the primary amino group are unsubstituted.

According to a further preferred feature, if $R_7$ signifies —COOM, this is in position ortho to the diazotizable primary amino group.

$R_{10}$ preferably signifies hydrogen.

$R_{11}$ advantageously signifies hydrogen, methyl, ethyl, hydroxyethyl or a radical of formula ($c_2$), in which $R_{13}$ preferably signifies hydrogen or carboxy.

The aliphatic acyl group Ac' advantageously signifies the radical of a low molecular aliphatic carboxylic acid, preferably of an alkanoic acid with 2 to 4 carbon atoms, more preferably acetyl or propionyl, of which acetyl is preferred.

In formula ($a_2$) preferably at least one of $Rx_5$ and $R_{16}$ has a significance other than hydrogen, more preferably $R_{13}$ has a significance other than hydrogen and $R_{15}$ signifies hydrogen, a nitro group or a sulpho group.

The primary amino group in formula ($a_4$) may be in any of the positions α and β of the naphthalene ring and, if m signifies 1, the sulpho group may be in any of the other available positions, preferably so that at least one vicinal position to the amino group is unsubstituted, e.g. if the amino group is in position 1, the sulpho group is preferably in any of the positions 3 to 8, more preferably 4 to 8, and if the amino group is in the position 2, the sulpho group is e.g. in position 1 or in any of the positions 4 to 8, more preferably 5, 6 or 7.

The compounds ($a_e$) are indicated in the free amine form; as diazo components they are however usually employed directly in the form of the respective commercially available diazonium compounds 1-diazonium-2-naphthol-4-sulphonic acid (in which r=0) (=diazoxidic acid) and 1—diazonium-6-nitro-2—naphthol-4-sulphonic acid (in which r=1) (=nitrodiazoxidic acid).

If in formula ($m_1$) $R_{18}$ signifies —OH, —$NH_2$ or —NHAc' it is preferably in position meta to the group —$NH_2$; preferably the symbol $R_{18}$ signifies hydrogen.

In formula ($m_2$) the primary amino group may be in any of the positions α and β of the naphthalene nucleus; if q is 1 or 2, the respective sulpho groups may be in any of the available other positions. If p=0, q preferably signifies 1 and the respective sulpho group is preferably in one of the positions 4 to 8, with respect to the primary amino group being in one of the positions 1 and 2. If p=0 more preferably the amino group is in position 1 and the azo group in position 4, any q sulpho groups preferably being in any of the positions 5 to 8. If p=1 the hydroxy group and the amino group are preferably in the positions 1,6, 1,7 (with q preferably=1) or 1,8 (with q preferably=1 or 2, the q sulpho groups being more preferably located in q of the positions 3 to 6); the coupling position is preferably a position ortho or para to the hydroxy group.

$R_{19}$ is preferably the radical of a diazo component of the benzene series, in particular of formula ($a_1$), ($a_2$) or ($a_3$).

Preferably —$D_1$, in particular —$D_2$ resp —D', contains at least one hydrophilic substituent, preferably a substituent selected from the group consisting of —$SO_3M$, —$SO_2NR_{10}R_{11}$, —COOM and —$CONR_{10}R_{11}$, more preferably not more than one hydrophilic substituent per homocyclic aromatic nucleus.

According to a particular feature of the invention $D_2$—N=N—, in particular $R_{19}$—N=N—, contains a metallizable substituent in ortho-position to the azo group bound to —X— and also this —X— contains a substituent in ortho-position to the same azogroup, that is metallizable together with it.

Such metallizable compounds are in particular compounds of formula (IVa), or mixtures thereof, wherein
—$D_2$ signifies the radical of a diazocomponent (DK") of formula
$HZ_1$—$D_2'$—$NH_2$, or its modified derivative,
and
—X— signifies

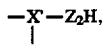

in which
—$Z_2H$ signifies —OH or —$NH_2$ and is in ortho-position to $D_2$—N=N—,
or, in the case of an (MK) of the type of formula (VIb), $D_2$—N=N— may also be in para-position to —$Z_2H$ and ortho-position to the sulphamoyl group, whose —NH-group in this case is also capable of metal complex formation.

They may be represented by the following formula

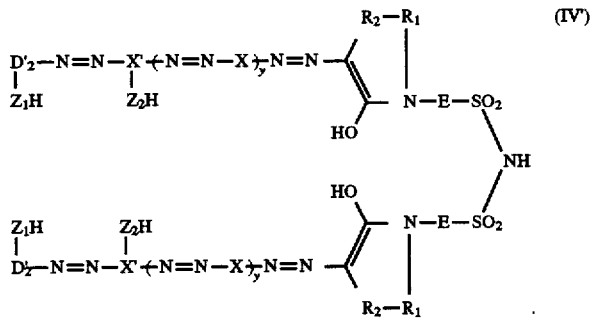

(IV')

These dyes, more particularly also the above metallizable dyes, may be directly used for dyeing, as described in more detail below, or may be converted to the respective metal complexes by metallization with complex-forming metal compounds, optionally in combination with further complex-forming ligands H-Lg'-H, and optionally with further reactions. Where according to the preferred mode, the metallizable dyes contain more than one, in particular two metallizable azogroups, the metal complexes derived therefrom may contain one or more covalently bound complex-forming metal atoms, depending also on the co-ordination number and valence thereof and on the presence or absence of further complex-forming ligands H-Lg'-H.

The ligand H-Lg'-H may be any chromophoric or non-chromophoric ligand or group of ligands, e.g. non-chromophoric ligands such as molecules of co-ordinatively linked water, ammonia, aliphatic polyamines (e.g. ethylene diamine or diethylene triamine) or hydroxycarboxylic acids (e.g. tartaric or salicylic acid), or chromophoric ligands such as a molecule of a metallizable azocompound, e.g. of the formula

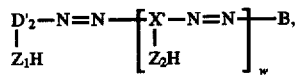

(X)

wherein
B is the radical of a coupling component H—B
and
w is 0, 1 or 2

The complex-forming metal may be any suitable metal, in particular chromium, cobalt, iron, copper, nickel, manganese, titanium, zirconium (also zirconyl) or/and aluminium, of which are preferred chromium, cobalt, iron, nickel and copper, before all complex-forming metals capable of forming 1:2 complexes with metallizable monoazodyes, especially chromium, cobalt and/or iron optionally in combination with minor proportions of aluminium, among which those with higher co-ordination number, mainly cobalt and iron, are particularly preferred.

The coupling component H—B may be any coupling component, in particular mono-coupling component, conventional per se in azo dyes, e.g. cyclic ones or open-chain methylene-active ones. Preferred coupling components H—B are of the formulae

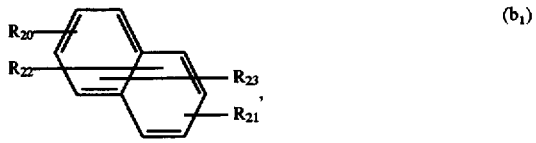 (b₁)

 (b₂)

 (b₃)

 (b₄)

 (b₅)

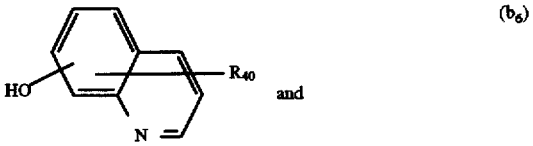 (b₆)

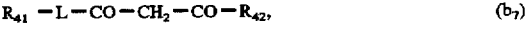 (b₇)

wherein
$R_{20}$ signifies hydrogen, —$OR_{24}$ or —$NHR_{24}$,
$R_{21}$ signifies hydrogen, —$OR_{24}$ or —$NHR_{24}$, at least one of $R_{20}$ and $R_{21}$ having a significance other than hydrogen,
$R_{22}$ signifies hydrogen, —$S_3M$, —$SO_2NR_{10}R_{11}$, —COOM or —$CONR_{10}R_{11}$,
$R_{23}$ signifies hydrogen, —$SO_3M$, —$SO_2NR_{10}R_{11}$, —COOM or $CONR_{10}R_{11}$,
$R_{24}$ signifies hydrogen, $C_{1-4}$-alkyl, Ac" or a radical of formula

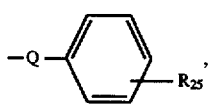

Ac" signifies the acyl radical of an aliphatic carboxylic acid, —Q— signifies —CO— or —SO$_2$—, R$_{25}$ signifies hydrogen, methyl, —NH—Ac', —COOM or —NO$_2$, R$_{26}$ signifies —OH or —NH$_2$, R$_{27}$ signifies hydrogen, C$_{1-4}$-alkyl, C$_{1-4}$-alkoxy, —OH, —NR$_{29}$R$_{30}$ or —NH—Ac', R$_{28}$ signifies hydrogen, C$_{1-4}$-alkyl or C$_{1-4}$-alkoxy, R$_{29}$ and R$_{30}$, independently, signify hydrogen, C$_{1-2}$-alkyl or C$_{2-3}$-hydroxy-alkyl, R$_{31}$ signifies hydrogen, sulphonaphthyl or a radical of formula

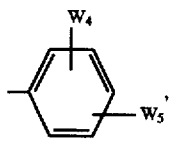

W$_4$ signifies hydrogen, halogen, methyl, methoxy or —COOM,

W$_5$ signifies hydrogen, halogen, trifluoromethyl, nitril, nitro, —COOM, —SO$_3$M or —SO$_2$NR$_{10}$R$_{11}$, R$_{32}$ signifies C$_{1-4}$-alkyl, phenyl, —COOM, —CONR$_{10}$R$_{11}$, —COOCH$_3$ or —COOC$_2$H$_5$, R$_{33}$ signifies =O or =NH, R$_{34}$ signifies hydrogen, unsubstituted amino, phenylamino, sulphonaphthyl, open-chain C$_{1-8}$-alkyl, C$_{6-9}$-cycloalkyl, carboxy-(C$_{1-4}$-alkyl), C$_{2-4}$-alkyl substituted with hydroxy, methoxy, ethoxy or a sulpho group in one of the positions β to Ψ, or a radical of formula (c$_4$), R$_{35}$ signifies hydrogen, nitril, acetyl, —COOM, carbamoyl, —SO$_3$M, pyridinio or 2-methyl-pyridinio, signifies hydrogen, hydroxy, methyl, carboxy, phenyl, sulphomethyl or carbamoyl, R$_{37}$ signifies hydroxy, primary amino, nitrilamino, thiol or a radical of formula

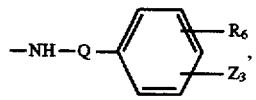

R$_{38}$ signifies hydroxy or primary amino,

R$_{39}$ signifies hydroxy or primary amino,

R$_{40}$ signifies hydrogen, methyl, chlorine, chloromethyl or chloroacetyl, —L— signifies —O—, —NH— or the direct bond, R$_{41}$ signifies naphthyl, sulphonaphthyl or disulphonaphthyl or a radical of formula (c$_4$), R$_{42}$ signifies C$_{1-4}$-alkyl, Z$_3$ signifies —NH$_2$, —NHAc' or —NO$_2$
and, where in formula (b$_4$) R$_{35}$ stands for pyridinio or orthomethylpyridinio, an acid group present in the molecule may be in the form of the respective anion (e.g. a sulpho group in the form of —SO$_3^-$) to form the counterion in the form of the inner salt.

The aliphatic acyl radical Ac" in the significance of R$_{20}$ may be the radical of any aliphatic carboxylic acid as can be introduced by acylation, in particular of a C$_{2-12}$-alkanoic, primary, monocarboxylic acid, preferably such as stated above for Ac', especially C$_{2-4}$-alkanoyl, most preferably acetyl.

If R$_{25}$ signifies —COOM, —Q— in formula (c$_3$) signifies in particular —CO—. If in formula (c$_3$) —Q— signifies the direct bond, R$_{25}$ preferably signifies hydrogen. If in formula (c$_3$) —Q— signifies —SO$_2$—, R$_{25}$ preferably signifies methyl, acetylamino or —NH$_2$. If in formula (c$_3$) —Q— signifies —CO—, R$_{25}$ preferably signifies hydrogen or —NO$_2$.

In formula (b$_1$) —OR$_{24}$ preferably signifies hydroxy and —NHR$_{24}$ preferably signifies —NHR$_{24}$', where R$_{24}$' signifies hydrogen, methyl, acetyl or a radical of formula (c$_3$). Preferably R$_{21}$ signifies hydroxy or —NHR$_{24}$' and R$_{20}$ signifies hydrogen or, where R$_{21}$ signifies —OH, also a group —NHR$_{24}$'. More preferably either R$_{21}$ signifies hydroxy and R$_{20}$ signifies hydrogen or —NHR$_{24}$' or R$_{21}$ signifies —NHR$_{24}$' and R$_{20}$ signifies hydrogen. R$_{22}$ preferably signifies hydrogen, —SO$_3$M, —COOM or —CONH$_2$. R$_{23}$ preferably signifies hydrogen or —SO$_3$M, more preferably hydrogen.

If in formula (2) R$_{27}$ signifies hydroxy, —NR$_{29}$R$_{30}$ or —NH—Ac', it is preferably in meta-position to R$_{26}$ and R$_{28}$ preferably signifies hydrogen. If R$_{27}$ signifies C$_{1-4}$-alkyl or C$_{1-4}$-alkoxy it may be in any of the available positions ortho, meta and para to R$_{23}$. More preferably R$_{26}$ signifies hydroxy. Advantageously R$_{28}$ signifies hydrogen.

Of the alkyl and alkoxy radicals with 1 to 4 carbon atoms, also in —B the lower molecular ones are preferred (analogously as in —D$_1$), more specifically ethyl, methyl, ethoxy and methoxy. In the C$_{2-3}$-hydroxyalkyl radicals the hydroxy group is preferably in β-position.

In formula (b$_3$) R$_{31}$ preferably signifies a radical of formula (c$_4$). In formula (c$_4$)—in the significance of R$_{31}$ —preferably at least one of W$_4$ and W$_5$ signifies hydrogen, more preferably W$_4$. R$_{32}$ preferably signifies C$_{1-4}$-alkyl, more preferably methyl. R$_{33}$ preferably signifies oxygen.

The open-chain C$_{3-8}$-alkyl radicals in the significance of R$_{34}$ may be linear or branched, if they contain 6 to 8 carbon atoms they are preferably branched; the cycloalkyl radicals in the significance of R$_{34}$ are preferably cyclohexyl, which may be substituted with 1 to 3 methyl groups, more preferably it is unsubstituted cyclohexyl. The carboxy-substituted C$_{1-4}$-alkyl group preferably is carboxymethyl or β-carboxyethyl. The substituent (hydroxy, methoxy, ethoxy, sulpho) at the C$_{2-4}$-alkyl, in the significance of R$_{34}$, is preferably in β-position. If R$_{34}$ signifies a radical of formula (c$_4$) W$_4$ preferably signifies hydrogen and W$_5$ preferably signifies carboxy, sulpho or trifluoromethyl. Preferred significances of R$_{34}$ are hydrogen, a radical of formula (c$_4$), C$_{1-8}$-alkyl, C$_{2-3}$-hydroxyalkyl and C$_{6-9}$-cycloalkyl.

R$_{35}$ preferably signifies hydrogen, a sulpho group or one of the stated nitrogen-containing substituents.

R$_{36}$ preferably has a significance other than hydrogen, more preferably R$_{36}$ signifies methyl.

In formula (b$_5$) preferably at least one of R$_{38}$ and R$_{39}$ signifies hydroxy, more preferably both R$_{38}$ and R$_{39}$ signify hydroxy groups.

If in formula (b$_5$) R$_{37}$ signifies a radical of formula (c$_5$) —NH—Q— preferably signifies a group —NH—SO$_2$—.

In formula (b$_6$) the hydroxy group preferably is in position 8. If R$_{40}$ is other than hydrogen it is preferably in position para to the 8-positioned hydroxy group. R$_{40}$ preferably signifies hydrogen or methyl, more preferably hydrogen.

In formula (b$_7$) —L— preferably signifies —NH—. More preferably R$_{41}$ is unsubstituted phenyl and R$_{42}$ is preferably methyl.

The coupling component radical —B preferably contains up to three cycles (homocyclic rings, heterocyclic rings and optionally a cycloaliphatic ring —a naphthalene radical being calculated as two cycles), more preferably —B contains one or two of such cycles.

A particular feature of the invention is represented by the metal complexes of metallizable dyes of the invention having two metallizable sites, viz. two metallizable azo groups, such as those of the above formula (IV'), and where the complex-forming metal is capable of 1:2-complex formation with metallizable monoazo dyes, in particular the preferred complex-forming metals iron, chromium and cobalt. In these complexes the configuration of the metal complex, upon exhaustive complexation, may be open-end, mono- or polymeric as shown by the schematic formula (XI) below

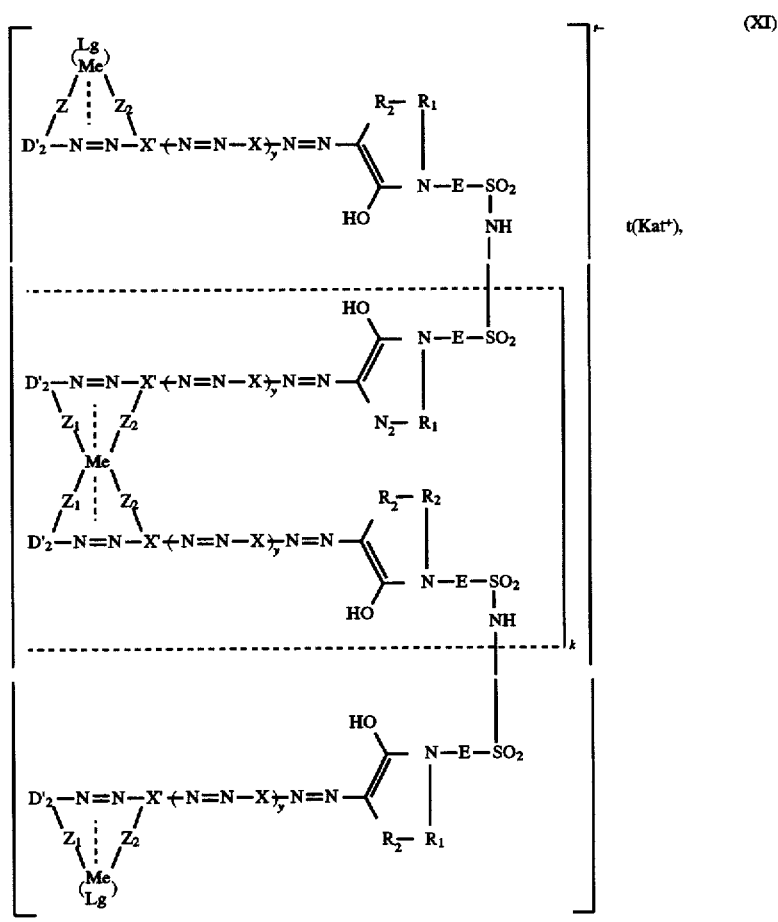

or cyclic, e.g. as shown by the formulae (XIa) and (XIb) below

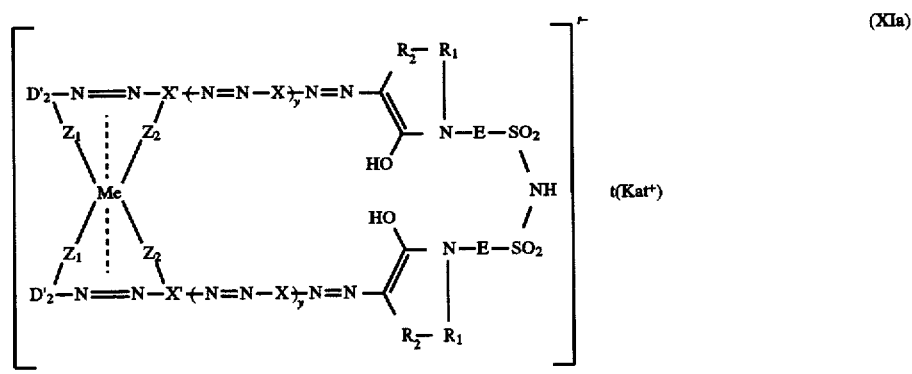

and (XIb)

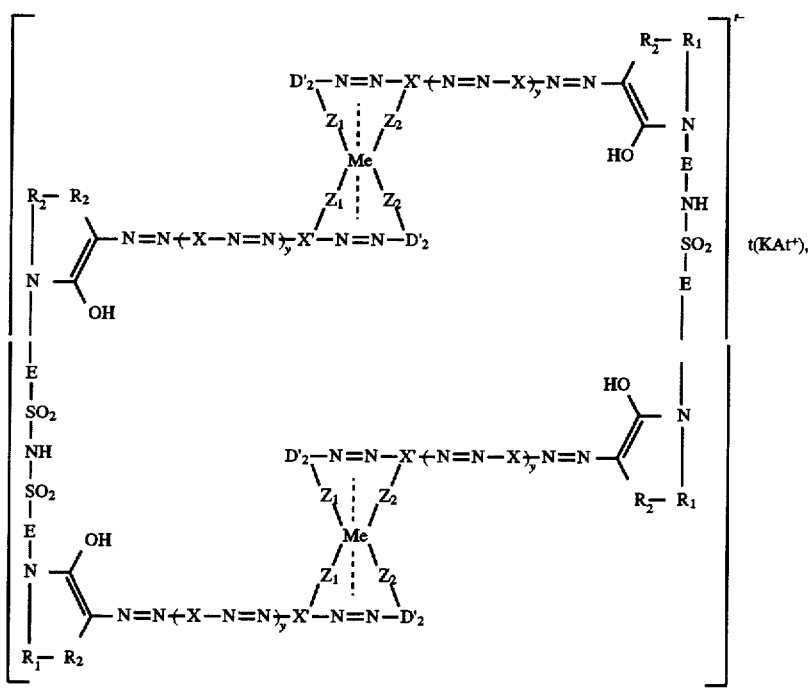

wherein $Z_1$ signifies —O— or —COO—, $Z_2$ signifies —O— or —NH—,

Lg signifies a ligand or group of ligands,

Me signifies a 1:2-complex-forming metal, preferably chromium, cobalt or iron, t is the total number of negative charges of the complex molecule, $Kat^+$ is a counterion, which is preferably non-chromophoric, and k in formula (XI) represents the number of the (repeating) complex units (KU), represented by the structure within the two lines of dashes, and may be zero or one or a number indicating the polymeric degree, e.g. 1 to 4

The more stable cyclic form is believed to be the one of formula (XIa), in particular in helical configuration of the polyazo complexant around the complex forming metal, as shown schematically by formula (XIa')

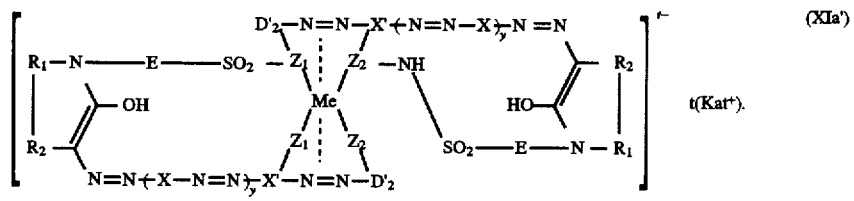

For the non-complexed tetra- to hexakisazodyes, i.e. those not containing a complexing metal, in particular not containing a metal Me, a similarly helical structure is assumed, i.e. as shown by the schematic following formula

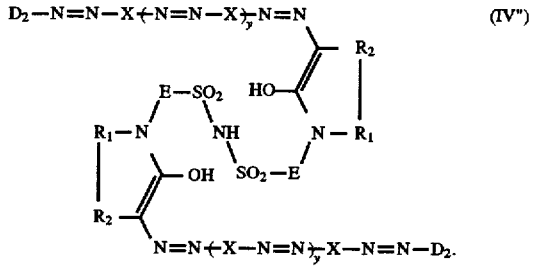

Lg is a complex-forming group, in particular as deriving from complexation with H-Lg'-H and optionally modification reactions, as required.

The number t depends on Me, Lg and the complexant of formula (IV') and may in particular be 0, 1 or 2 or more. If in any of the above metal complexes any of Lg, —B or/and —$D_2$'—contains a covalently bound cationic group, e.g. a pyridinium group as mentioned above, its positive charge may equilibrate at least in part a corresponding number of negative charges of the complex, so that t is reduced accordingly. It is however preferred that in the dye molecules of the invention the covalently bound anionic groups prevail. $Kat^+$ may be any cation as is formed in the synthesis of the respective dye and depends thus also on Lg and Me and further also on the complex forming reaction conditions (namely the pH and the employed solvent), or a cation introduced by ion exchange, e.g. an alkali metal cation or/and an ammonium cation; in the free acid form it is indicated as a hydronium ion $H_3O^+$.

The metal complexes stated above may be synthetized by reactions known per se, im particular diazotization, coupling and metallization and optionally further modification reactions as required; more particularly the process for the production of the metal complexes or mixtures stated above is characterized in that a) at least one metallizable compound of formula (IV), preferably (IV'), and optionally at least one further complex-forming ligand, e.g. H-Lg'-H, are reacted with a complex-forming metal compound, or b) a metal complex of at least one metallizable compound of formula (V') and optionally of at least one further ligand, is diazotized and coupled to at least one coupling component (BK) and optionally also to at least one coupling component H—B as defined above.

The metallization to metal complexes may be carried out in analogy to known metal complex formation reactions.

For the metallization of the compounds of formula (IV), resp. (IV'), or (V') and optionally H-Lg'-H there may be employed conventional suitable metal compounds, e.g. acetates or hydrosoluble salts of mineral acids, in particular chromium trichloride, cobalt dichloride, copper dichloride or sulphate, iron di- or trichloride, chromium trifluoride, manganese chloride, acetate or sulphate, aluminium chloride, titanium chloride, zirconium tetrachloride or sulphate, zirconyl chloride, cobalt sulphate or nitrate, iron-II- or -III-sulphate, chromium sulphate, chromium or cobalt acetate, potassium chromium sulphate, ammonium chromium sulphate (e.g. chrome alums) and optionally, with the addition of a reducing agent e.g. of glucose, also sodium or potassium chromate or bichromate.

The chromation may be carried out directly up to the 1:2—chromium complex stage or by degrees over the 1:1—chromium complex stage and then further complexation up to the 1:2—chromium complex stage.

Chromation may be carried out in aqueous medium, preferably at pH values in the range of 2 to 10 and temperatures in the range of 95° to 130° C., if necessary under superatmospheric pressure. Optionally the reaction may be carried out with addition of organic solvents or also only in organic solvents. Suitable organic solvents are preferably such that are miscible with water, have a boiling point above 100° C. and in which the azo dyes and the metal salts are soluble, e.g. glycols, ether alcohols or amides (e.g. ethylene glycol, polyethylene glycol, β-ethoxyethanol, β-methoxyethanol, formamide or dimethylformamide). For the stepwise production of 1:2—chromium complex compounds the chromation may be carried out gradually, synthetizing first the 1:1—chromium complex of one of the complexants or complexant portions of the molecule and from this with a second complexant or complexant portion of the molecule then the 1:2—complex. The 1:1—chromium complexes may be produced in conventional manner, e.g. under analogous conditions as for the 1:2—chromium complexes, but preferably under stronger acidic pH-values, advantageously at pH <3. It is also of advantage to synthesize 1:2—chromium mixed complexes by simultaneously metallizing different complexants of formula (IV), resp. (IV'), or (V') and optionally H-Lg'-H or to couple the diazocompound of a mixture of compounds of formula (V') to one or more coupling components (BK) and optionally H—B.

The metallization of azocompounds of formula (IV), resp. (IV'), or (V') to the corresponding iron-complexes, mainly 1:2—iron-complexes, may be carried out in conventional manner, suitably in aqueous medium, advantageously at pH-values in the range of 3.5 to 6.5, preferably 4 to 6, with heating. The metallization to iron complexes is advantageously carried out at temperatures in the range of 40° C. to reflux temperature, preferably 60° to 100° C.

The metallization of azocompounds of formula (IV), resp. (IV'), or (V') to the corresponding cobalt-complexes, mainly 1:2—cobalt-complexes, may be carried out in conventional manner, suitably in aqueous medium, advantageously at pH-values in the range of 9 to 12, preferably 10 to 11, optionally with heating. The metallization to cobalt complexes is advantageously carried out at temperatures in the range of 30° to 90° C., preferably 40° to 70° C.

The metallization to copper complexes is preferably carried out at pH 7 to 10 and at temperatures in the range of 60° to 100° C., preferably with copper sulphate.

Other metallizations may be carried out in analogous way, as conventional per se.

For the production of cyclic complexes, in particular those of formula (XIa) or (XIb), it is preferred to mix the bis-diazotized derivative of a bis-amine of formula

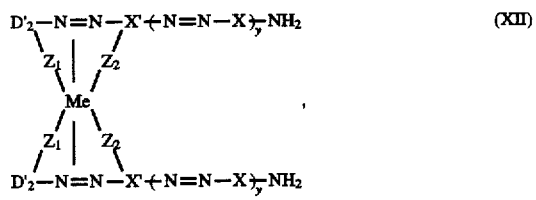

(XII)

in particular

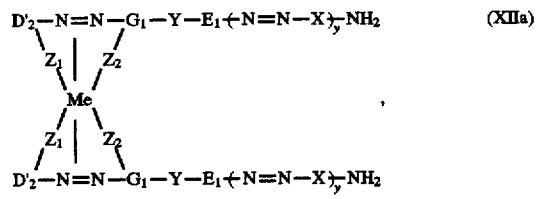

(XIIa)

with the solution of (BK) under acidic conditions, e.g. at a pH in the range of 1 to 6.5, preferably 1.5 to 6, and then to slowly increase the pH, e.g. by addition of NaOH or KOH solution, to the desired value suitable for coupling, e.g. between 6 and 11, preferably between 8 and 11. For the production of metal complexes of polymeric structure, in particular of formula (XI), it is preferred to add the solution of the bisdiazocompound into the solution of (BK) under distinctly basic conditions, as suitable for coupling, preferably at a pH in the range of 8 to 11.

By process variant a) there may be obtained cyclic Me-complexes or also mixtures of polymeric and cyclic Me-complexes.

Upon completion of the required coupling and optionally metallization or/and further optional modification reactions the obtained dye or mixture thereof may be isolated from the mother-liquor in a manner conventional per se, e.g. by salting out or by acidification with a strong mineral acid or e.g. by evaporation, if desired upon dialysis through a suitable membrane. If desired, the dye may, optionally upon isolation or dialysis, be blended with suitable blending agents conventional per se, e.g. alkali metal salts (sodium carbonate, sodium sulphate), non-electrolyte blending agents (mainly oligosaccharides, e.g. dextrines such as maltodextrose) or/and with anionic surfactants, preferably sulpho-group-containing surfactants, in particular hydrocarbon sulphonates, sulphonated castor oil, sulphosuccinates or lignine sulphonate. If a surfactant is employed the weight ratio of the surfactant to the dye is advantageously in the range of 5:95 to 40:60

If desired the dyes may be formulated with water as liquid concentrated dye-compositions. The liquid forms may be plain concentrated aqueous solutions of the dye or dye-mixture in water; if desired or required (depending on the solubility of the dye) a suitable formulation assistant may be added, in particular a hydrotrope, a solubilizer or/and a stabilizer, e.g. selected from dicyanodiamide, di- or triethanolamine, N-methylpyrrolidone, urea, caprolactam, low molecular glycols or glycolethers (e.g. mono- or diethyleneglycol or their mono-$C_{1-4}$-alkylethers), or a surfactant or other blending agent as described above. The dye content in the liquid concentrated compositions is e.g. in the range of 10 to 50, preferably 15 to 40% by weight. If a hydrotrope, solubilizer or stabilizer is added, it is employed advantageously in an efficient amount preferably in the range of 0.1% to 20% by weight, more preferably 0.5 to 5% by weight of the aqueous concentrated dye composition. The dry-substance content of the liquid concentrated dye compositions is advantageously in the range of 10 to 70%, preferably 20 to 50% by weight, referred to the weight of the composition.

The dyes of the invention advantageously contain at least one hyrosolubilizing group as stated above, in order to be readily hydrosoluble and serve as hydrosoluble dyes, especially, if they contain at least one anionic group, they serve as anionic dyes; they are suitable for the dyeing of substrates dyeable with hydrosoluble dyes, especially anionic dyes.

The dyes of the invention may be of any hue, depending on their components, in particular (DK) [more particularly (DK') or (DK"), and (MK) if any] and (BK) and, if present, Me and Lg, principally ranging from clear yellow shades to green shades and to red shades (including also bluish red shades, orange shades, brown shades and olive shades); there may, however, also be produced dyes of other shades, in particular ranging from blue shades to gray and to black shades (including also violet shades).

Any substrate that is dyeable with hydrosoluble dyes, in particular with anionic dyes, is suitable as a substrate that may be dyed with the azo dyes resp. metal complexes of the invention; these include natural and regenerated cellulose, polyurethanes, basically modified high polymers (e.g. basically modified polypropylene), natural or synthetic polyamides or anodized aluminium, in particular, however, leather substrates. The substrate to be dyed may be in any conventional form, e.g. in the form of loose fibres, filaments, yarns, woven or knitted goods, non-woven webs, carpets, half-ready-made and ready-made soft goods and tanned leather or pelts. The dyes may be employed in any desired concentration up to the saturation of the substrate. The dyeing may be carried out by any conventional methods that are suitable for the substrate to be dyed, e.g. by exhaustion or impregnation methods (e.g. padding, spraying, foam application or application with a roller, or printing), preferably from aqueous medium; for synthetic substrates, the dye may optionally also be incorporated into the synthetic mass. Paper may be dyed in the pulp or after sheet formation.

The dyes of the invention are, however, mainly suitable for the dyeing of leather and pelts.

Any kinds of leather which are conventionally dyed from aqueous medium are suitable, particularly grain leather (e.g. nappa from sheep, goat or cow and box-leather from calf or cow), suede leather (e.g. velours from sheep, goat or calf and hunting leather), split velours (e.g. from cow or calf skin), bukskin and nubuk leather; further also woolled skins and furs (e.g. fur-bearing suede leather). The leather may have been tanned by any conventional tanning method, in particular vegetable, mineral, synthetic or combined tanned (e.g. chrome tanned, zirconyl tanned, aluminium tanned or semi-chrome tanned). If desired, the leather may also be re-tanned; for re-tanning there may be used any tanning agent conventionally employed for re-tanning, e.g. mineral, vegetable or synthetic tanning agents [e.g. chromium, zirconyl or aluminium derivatives, quebracho, chestnut or mimosa extracts, aromatic syntans, polyurethanes, (co) polymers of (meth)acrylic acid compounds or melamine/, dicyanodiamide/and/or urea/formaldehyde resins]. Thus leathers of very high to very low affinity for anionic dyes may be used.

The leathers may be of various thicknesses, thus, there may be used very thin leathers, such as book-binder's leather or glove-leather (nappa), leather of medium thickness, such as shoe upper leather, garment leather and leather for handbags, or also thick leathers, such as shoe-sole leather, furniture leather, leather for suitcases, for belts and for sport articles; woolled leathers and furs may also be used. After tanning (in particular after a re-tanning) and before dyeing, the pH of the leather is advantageously set to values in the range of 4 to 8 (the leather is "neutralized"); depending on the kind of the leather, there may be chosen an optimum pH range, e.g. for grain leather pH values in the range of 4 to 6, for suede leather and split velours and for very thin leathers pH-values in the range of 4.5 to 8, for intermediately dried suede leathers and intermediately dried split velours the pH may range in the scope of 5 to 8. For the adjustment of the pH-value of the leather there may be employed conventional assistants; for tanned leather of acidic character the pH may be adjusted by addition of suitable bases, e.g. ammonia, ammonium bicarbonate or alkali metal salts of weak acids, e.g. sodium formate, sodium acetate, sodium bicarbonate, sodium carbonate or sodium bisulfite, of which sodium formate and ammonia are preferred. Sodium carbonate and sodium bicarbonate are usable in particular as second bases for the exact adjustment of the superficial pH-value of the leather. Mineral tanned leather may, if desired, also be masked, e.g. with alkali metal formate, oxalate or polyphosphate or e.g. with titanium/potassium oxalate.

The dyeing may be carried out in a manner known per se suitably in an aqueous medium and under conventional temperature and pH conditions, in particular in the temperature range of 20° to 80° C., preferably 25° to 70° C., milder temperature conditions, in particular in the range of 25° to 40° C., being preferred for the achievement of deeper penetrations and for the dyeing of woolled skins and furs. The pH-values of the dye-bath may, in general, range broadly, mainly from pH 8 to pH 3; in general the dyeing may be advantageously begun at higher pH-values and concluded at lower pH-values.

Preferably the dyeing is carried out at pH-values ≧4, in particular in the range of 8 to 4, and for the conclusion of the dyeing procedure the pH-value is lowered (e.g. by addition of an acid conventional in the leather dyeing technique such as acetic acid or formic acid) preferably to values in the range between 4 and 3. The dye concentration may range broadly, if desired up to the saturation degree of the substrate, e.g. up to 5 % referred to the wet weight of the substrate. The dyeing may be carried out in one or more stages, e.g. in two stages, optionally with insertion of charge reversal of the substrate by means of conventional cationic assistants. The dyes of the invention may, if desired, be employed in combination with conventional dyeing assistants, mainly non-ionic or anionic products (in particular surfactants, preferably hydrophilic polysaccharide derivatives, polyoxyethylated alkylphenols or alcohols, lignosulphonates or sulpho-group-containing aromatic compounds).

A fatting may, if desired, be carried out before and/or after the dyeing process, in particular also in the same liquor. For fatting after the dyeing process the fatting agent is advantageously added before the pH of the liquor is lowered, preferably to values between 3 and 4.

For the fatting (in particular fat-liquoring) step there may be used any conventional natural animal, vegetable or mineral fat, fat oil or wax, or chemically modified animal or vegetable fat or oil, which include in particular tallow, fish oils, neats-foot oil, olive oil, castor oil, rapeseed oil, cottonseed oil, sesame oil, corn oil and japanese tallow and chemically modified products thereof (e.g. hydrolysis, transesterification, oxidation, hydrogenation or sulphonation products), bees-wax, chinese wax, carnauba wax, montan wax, wool fat, birch oil, mineral oils with boiling range within 300° and 370° C. (particularly the so-called "heavy alkylates"), soft paraffin, medium paraffin, vaseline and methyl esters of $C_{14-22}$-fatty acids, and synthetic leather fatting agents, including esters, in particular partial esters of polybasic acids (e.g. phosphoric acid) with optionally oxyethylated fatty alcohols. Of the above mentioned the methyl esters, the sulphonation products and the phosphoric acid partial esters are particularly preferred. By the term "sulphonation" for the fatting agents, there is meant generally the introduction of the sulpho group including also the formation of a sulphato group (="sulphating") and the introduction of a sulpho group by reaction with a sulphite or $SO_2$ (="sulphiting").

A conventional leather softener, in particular a cationic leather softener may, if desired, be applied in a final steps particularly if fatting has been carried out with a sulphonated fat-liquoring agent.

The treated substrate may then be further treated in conventional manner, e.g. rinsed or washed, drained, dried and cured.

When a dye (AZ) or a mixture thereof or preferably a dye ($AZ_1$) or a mixture thereof as defined above, especially a non-metallized polyazodye of the above formula (IV) [in particular (IVa), (IVb) or (IVc)] or (IV'), is employed, preferably in the non-metallized form, for dyeing, in particular for the dyeing of leather, it is also of advantage to combine it with a corresponding azodye (BZ) of an inferior number of azogroups and that does not contain a radical of a bis-coupling component (BK) but contains the radical of a mono-coupling component H—B.

The invention thus provides also a dye mixture comprising a dye (AZ) or a mixture thereof and a dye (BZ) or a mixture thereof.

As dyes (BZ) there may be employed known dyes or dyes obtainable by processes that are analogous to known methods. They are in particular obtainable by coupling the diazocompound of a diazocomponent of formula $D_1'$—$NH_2$ or a mixture thereof to at least one coupling component H—B and optionally further modification reactions.

The dyes (BZ) are preferably non-metallized dyes and correspond more preferably to the formula $$D_2-N=N+X-N=N+_wB, \qquad (XIII)$$

e.g. to formula (X). It is especially advantageous to combine at least one dye (AZ) resp. ($AZ_1$) with at least one dye (BZ) of the same or a very similar shade. This is with particular advantage brought about by using the same (DK) [more particularly the same (DK') or (DK") and the same (MK) if any] and as H—B a coupling component of formula

wherein the symbols —$R_1$—$R_2$— and —E—, independently from formula (Ia), have one of the significances stated above, $W_5$ has the significances indicated above and the carbon indicated by the asterisk * is capable of being coupled with a diazonium compound. It is, however, preferred that the symbols —$R_1$—$R_2$— and —E— have each the same significance as the respective symbol in the combined dye of formula (IV). In formula (XIV) $W_5$ signifies preferably —COOM, —$SO_3M$, —$SO_2NR_{10}R_{11}$ or —H.

By the combination of dyes (AZ) and (BZ), in particular of formula (IV) and (XIII), of the same or similar shade there may be achieved a very homogeneous colour distribution in depth (dye penetration) and on the surface of leathers of any affinity character, in particular also on leathers of low affinity for anionic dyes. The molar ratio of dye (AZ), preferably of formula (IV), or mixture thereof, to dye (BZ), preferably of formula (XIII), or mixture thereof, may be in any range that leads to the desired properties, e.g. in the range of 1:10 to 10:1, preferably 1:5 to 3:1, more preferably 1:4 to 2:1. With these mixtures there may also be achieved an optimum solubility in water, so that liquid compositions of high dye concentration can be produced.

The mixtures of (AZ) and (BZ)may be produced by admixing the respective components (AZ) and (BZ), e.g. by conventional dye-mixing techniques. Mixtures of (AZ) and (BZ) deriving from the same (DK) [more particularly the same (DK') or (DK") and the same (MK) if any]may advantageously be produced by coupling the required diazocompound or mixture thereof, preferably the diazocompound of an amine $D_1'$—$NH_2$ or a mixture thereof, to a mixture of (BK) and H—B.

According to the invention there may be obtained azodyes and metal complex dyes that display, even with a relatively low number of hydrosolubilizing substituents in —A, —$D_1$ and optionally —X— or/and optionally Lg or —B, a high solubility in water, especially where anionic dyes are in alkali metal salt form; they are distinguished by their stability to electrolytes (in particular inorganic ions), specifically also to bases and acids, and are also distinguished, especially on leather, by their build-up and a high degree of insensitivity to variations of the affinity of the leather towards anionic dyes, very level dyeings of outstanding penetration and high colour-yield being obtainable. The dyeings particularly on leather, especially those obtained with metal complexes, have excellent fastness properties, for example wet-fastnesses, fastness to rubbing, light-fastness and stability to PVC-migration. They are readily combinable with other dyes, in particular such with similar tinctorial behaviour. There may be obtained very level, intense, fine dyeings, grain side and velours side being very evenly dyed, the shade of the dyeings on different kinds of leather being equal or very similar; in admixture with corresponding compatible dyes with which the dyes of the invention are combinable, there may also be obtained very intense and regular dyeings of high yield and optimum fastnesses. By the choice of the substituents some of the properties of the dyes (e.g. solubility, shade, build-up, penetration, levelness etc.) may be varied accordingly. The metal-free polyazodyes of the invention, in particular the non-metallized tetra- to hexakisazo dyes, especially the preferred ones, are also well combinable with metal complex dyes, in particular 1:2—metal complexes of disazo or trisazo dyes and also with metal-free trisazo or tetrakisazo dyes, there being obtainable very homogeneous shades and penetrations and regular dyeings of optimum fastnesses, also light fastness.

In the following Examples parts and percentages are, if not otherwise indicated, by weight; parts by weight relate to parts by volume as grams to milliliters. The temperatures are indicated in degrees Celsius. Where not otherwise indicated, for the lowering of the pH or setting acidic pH values there is added an aqueous 30 % solution of hydrochloric acid and for increasing the pH or setting alkaline pH values there is added an aqueous 30% sodium hydroxide solution. In the Application Examples the respective dyes are used in blended form containing 30 % of the respective dye and the blending agent being Glauber's salt (sodium sulphate), the other products employed in the Application Examples are commercially available products conventional in the treatment of leather.

Examples of the production of (BK)

(BK1) 142 parts of disulphanilamide [synthetized as described by M. L. CROSSLEY et al. in JACS 60 (1938), 2222–2224, or as described below] are diazotized in conventional ray in acidic medium and the obtained solution of the bisdiazocompound is added dropwise to a solution of 56 parts of sodium bisulphite and 169 parts of sodium sulphite in 650 parts of water, keeping the pH between 6 and 7 with 150 parts of an aqueous 25% sodium hydroxide solution. When the reduction is complete, i.e. when no more bisdiazo compound can be detected, 215 parts of an aqueous 30% hydrochloric acid solution are added and the suspension is heated to 90° C. for 3 hours. Then the pH is adjusted to 1.5 by addition of an aqueous 25% sodium hydroxide solution and 88 parts of acetoacetamide are added. When the cyclisation reaction is completed the suspension is filtered. There are obtained 150 parts of the bis-coupling component of formula

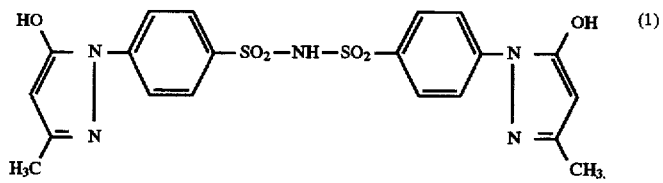

The disulphanilamide may be synthetized as follows:

86 parts of 4—aminobenzenesulphonamide are suspended in 500 parts of water at 55° C. 65 parts of acetic acid anhydride are added over 1 hour, keeping the pH at 3.5 with 5 parts of aqueous 25% sodium hydroxide solution. The pH is then increased to 11 and 270 parts of N-acetylsulphanilyl chloride are added slowly, keeping the pH between 10 and 10.5 with 300 parts of aqueous 25% sodium hydroxide solution. The acetyldisulphanilamide is hydrolyzed by the addition of 800 parts of aqueous 25% sodium hydroxide solution and heating at 75° C. for 3 hours. The produced disulphanilamide is finally isolated at pH 2 at 40° C.

(BK2) 32.7 parts of disulphanilamide are dissolved in 300 parts of water at a pH in the range of 6 to 7, with 4 parts of an aqueous 25% sodium hydroxide solution. This solution is heated to 50–60° C. and 19 parts of diketene are added during 30 minutes. The reaction is continued for 2 hours at the same temperature. The obtained bisacetoacetyl intermediate of formula

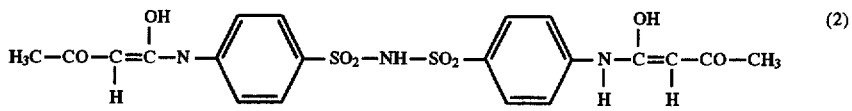

is suspended in 200 parts of methanol. 20 parts of methylanoacetate, 2 parts of piperidine and 2 parts of acetic acid are added and the suspension is heated under reflux until cyclisation is complete. When the reaction is completed methanol is replaced by water by simultaneous distillation and addition of water. The obtained product of formula

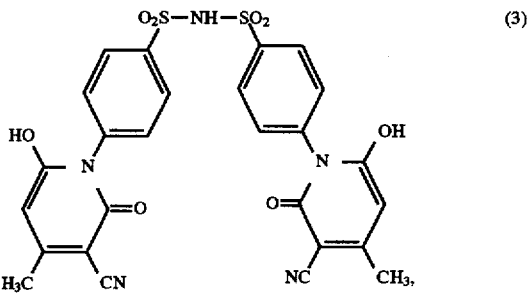

may be used directly or may be isolated by acidification to pH 2 and filtration.

Examples of middle components (MK)

(MK1): 2-sulphanilylamino-3H-pyrimidine-4,6-dione.

(MK2): 6-amino-2—sulphanilylamino-3H-pyrimidine-4-one.

(MK3): 4,6-diamino-2-sulphanilylamino-pyrimidine synthetized as follows:

23 parts of 4-amino-benzenesulphonylguanidine (="sulfaguanidine") are added to 100 parts of a 30% solution of sodium methylate in methanol. The mixture is heated to 50° C. and 15 parts of malononitrile are added slowly. Then the mixture is heated to reflux for 1 hour. Once the cyclization reaction is completed and after the addition of 100 parts of water, methanol is distilled off by increasing the temperature to 95° C. Finally the pH is decreased to 5 by addition of 22 parts of a 30% hydrochloric acid solution and the product is isolated by filtration at 80° C.

(MK4): 4-amino-N-(3'-hydroxyphenyl)-benzenesulphonamide.

(MK5): 1-(4'-aminophenyl)-3-methyl-5-pyrazolone.

(MK6): 1-(4'-aminophenyl)-3-methyl-5-aminopyrazole.

(MK7): 1-(3'-aminophenyl)-3-methyl-5- pyrazolone.
(MK8): 6-amino-1-naphthol-3-sulphonic acid (J-acid).

The diazo components employed in the following Examples are (DK1): anthranilic acid;

(DK2): metanilic acid;

(DK3): orthanilic acid;

(DK4): sulphanilic acid;

(DK5): 2-amino-5-sulphobenzoic acid;

(DK6): 2-amino-4-sulphobenzoic acid;

(DK7): sulphanilamide;

(DK8): diazoxidic acid;

(DK9): 1-amino-2-hydroxy-3-nitro-5-benzenesulphonic acid;

DK10): 1-amino-2-hydroxy-5-benzenesulphonic acid amide.

dissolved in 50 parts of water and 20 parts of an aqueous 25% sodium hydroxide solution, keeping the pH at 9% addition of an aqueous 25% sodium hydroxide solution, at a temperature of 10° C. When the coupling reaction is completed the suspension is acidified by addition of 50 parts of an aqueous 30% hydrochloric acid solution. 7.6 parts of sodium nitrite previously dissolved in 50 parts of water are added dropwise. When the diazotization reaction is completed 24.4 parts of (BK1) dissolved in 50 parts of water and 16 parts of an aqueous 25% sodium hydroxide solution are added and the pH is raised to 9 by addition of an aqueous 25% sodium hydroxide solution. When the coupling reaction is completed the obtained dye is salted out by addition of sodium chloride. It dyes leather in yellow shades and corresponds in the form of the free acid to the formula

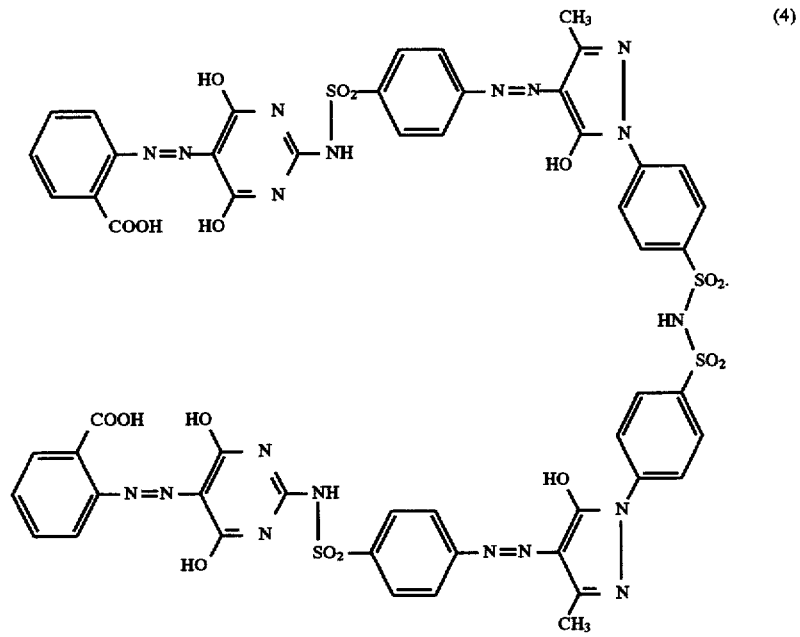

EXAMPLES OF AZODYES AND METAL COMPLEXES

Example 1

13.7 parts of (DK1) are diazotized in conventional way with $NaNO_2$ in the presence of hydrochloric acid and coupled to 28.2 parts of (MK1), which are previously

Example 2

The procedure of Example 1 is repeated, with the difference that instead of (DK1) there are used 17.3 parts of (DK2).

The obtained dye dyes leather in yellow shades and corresponds in the form of the free acid to the formula

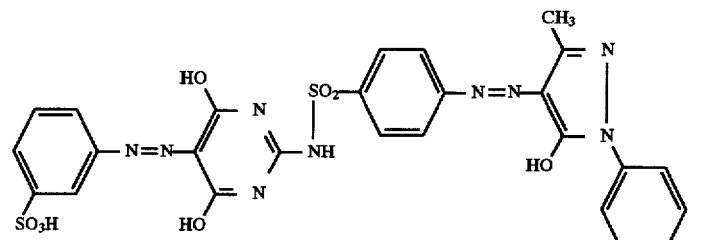

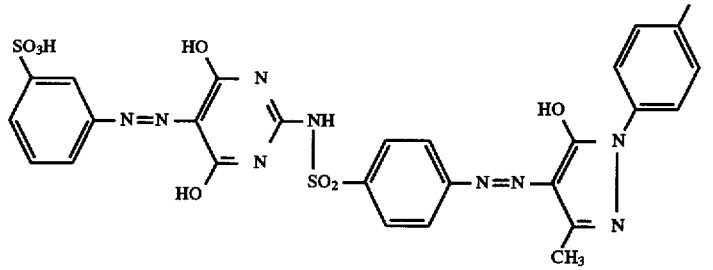

(5)

Example 3

The procedure described in Example 1 is repeated, with the difference that instead of the bis-coupling component (BK1) there is employed the equivalent amount of the bis-coupling component (BK2). The obtained dye dyes leather in yellow shades.

Example 4

The procedure described in Example 1 is repeated, with the difference that instead of the middle component (MK1) there is employed the equivalent amount of the middle component (MK2). The obtained dye dyes leather in yellow shades.

Example 5

The procedure described in Example 1 is repeated, with the difference that instead of the middle component (MK1) there is employed the equivalent amount of the middle component (MK3). The obtained dye dyes leather in yellow shades.

Example 6

The procedure described in Example 1 is repeated, with the difference that instead of the middle component (MK1) there is employed the equivalent amount of the middle component (MK5). The obtained dye dyes leather in orange shades.

Example 7

The procedure described in Example 1 is repeated, with the difference that instead of the middle component (MK1) there is employed the equivalent amount of the middle component (MK6). The obtained dye dyes leather in orange shades.

Example 8

The procedure described in Example 1 is repeated, with the difference that instead of the middle component (MK1) there is employed the equivalent amount of the middle component (MK7). The obtained dye dyes leather in orange shades.

Example 9

The procedure described in Example 1 is repeated, with the difference that in place of 13.7 parts of (DK1) there is used a mixture of 6.8 parts of (DK1) and 8.7 parts of (DK2). The obtained dyestuff dyes leather in yellow shades. It is a mixture that, in the form of the free acid contains the dye of formula (4) stated in Example 1, the dye of formula (5), stated in Example 2 and the dye of the following formula

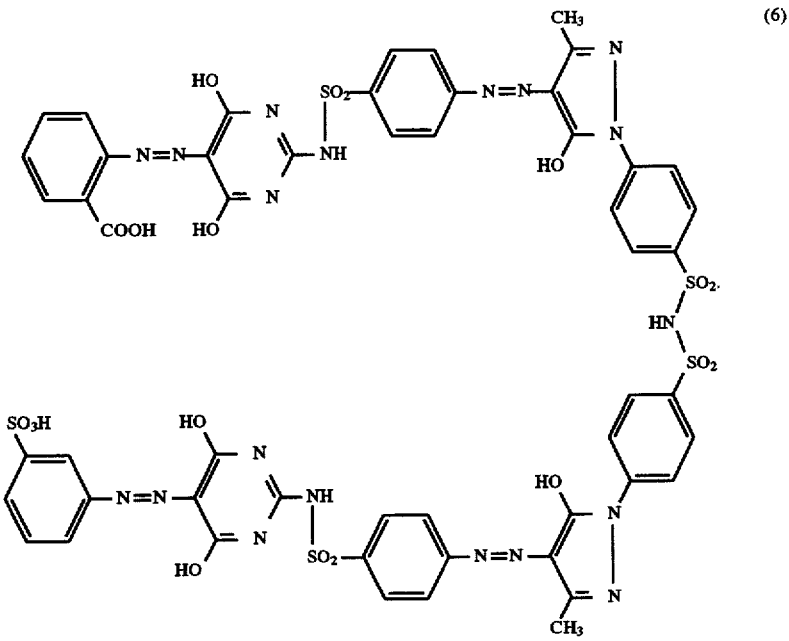

(6)

in statistical distribution.

Example 10

The procedure described in Example 2 is repeated, with the difference that in place of (DK2) there is employed the same amount of (DK3). The obtained dye dyes leather in clear yellow shades.

Example 11

The procedure described in Example 2 is repeated, with the difference that in place of (DK2) there is employed the same amount of (DK4). The obtained dye dyes leather in clear yellow shades.

Example 12

The procedure described in Example 1 is repeated, with the difference that in place of (DK1) there is employed the equivalent amount of (DK5). The obtained dye dyes leather in clear yellow shades.

Example 13

The procedure of Example 12 is repeated, with the difference that instead of (DK5) acid there is employed the same amount of (DK6). The obtained dye dyes leather in clear yellow shades.

Example 14

The procedure described in Example 1 is repeated, with the difference that instead of (DK1) there is employed the equivalent amount of (DK7). The obtained dye dyes leather in clear yellow shades.

Example 15 a) 25 parts of (DK8) are dissolved in 50 parts of water at pH 6 and coupled to 28.2 parts of (MK1), which are previously dissolved in 50 parts of water and 20 parts of an aqueous 25% sodium hydroxide solution, keeping the pH at 9 by addition of an aqueous 25% sodium hydroxide solution. When the coupling reaction is completed the monoazo suspension is acidified with 50 parts of an aqueous 30% hydrochloric acid solution and 7.6 parts of sodium nitrite, previously dissolved in 50 parts of water, are added dropwise. When the diazotization reaction is completed 24.4 parts of (BK1), dissolved in 50 parts of water and 60 parts of an aqueous 25% sodium hydroxide solution, are added keeping the pH at 11 by addition of an aqueous 25% sodium hydroxide solution. Upon completion of the coupling reaction there is obtained the tetrakisazo dye, which dyes leather in bordeaux shades and which in the free acid form corresponds to the following formula

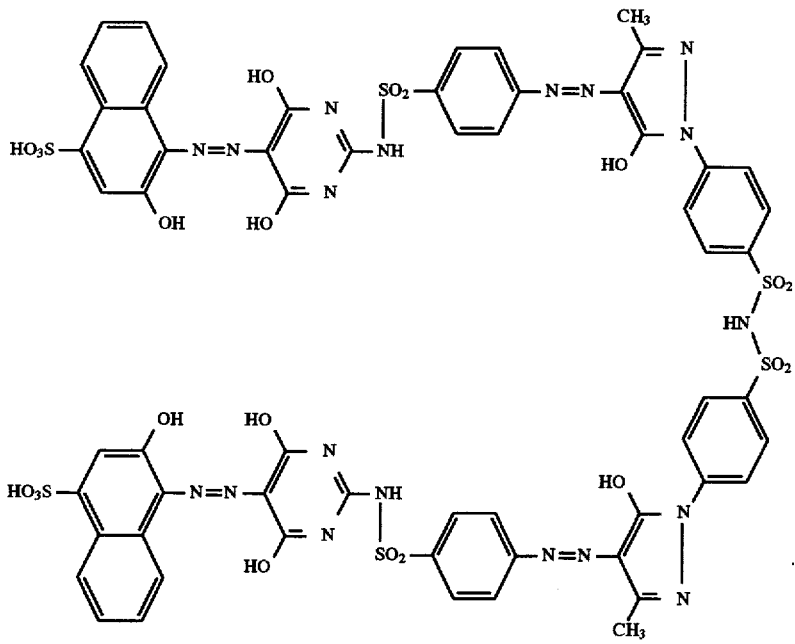

(7)

This dye may be either isolated by salting-out and filtering or may be further reacted according to the following part b).

b) When the coupling reaction is completed the solution is heated to 50° C., 12 parts of cobalt sulphate heptahydrate and 4 parts of hydrogen peroxide are added thereto. When the cobaltation reaction is completed the dye is salted out and filtered. It dyes leather in brown bordeaux shades. It may be represented in the form of the free acid by the following formula cobalt sulphate there is employed the equivalent amount of chromium alum and the chromation is carried out at pH 5 and at 100° C. The obtained chromium complex dyes leather in bordeaux shades.

Examples 16 and 16bis

The procedure described in Examples 15 and 15bis is repeated, with the difference that instead of (DK8) there is employed the equivalent amount of (DK9). The obtained cobalt complex (Example 16) dyes leather in brown-bordeaux shades and the obtained chromium complex (Example 16bis) dyes leather in bordeaux shades.

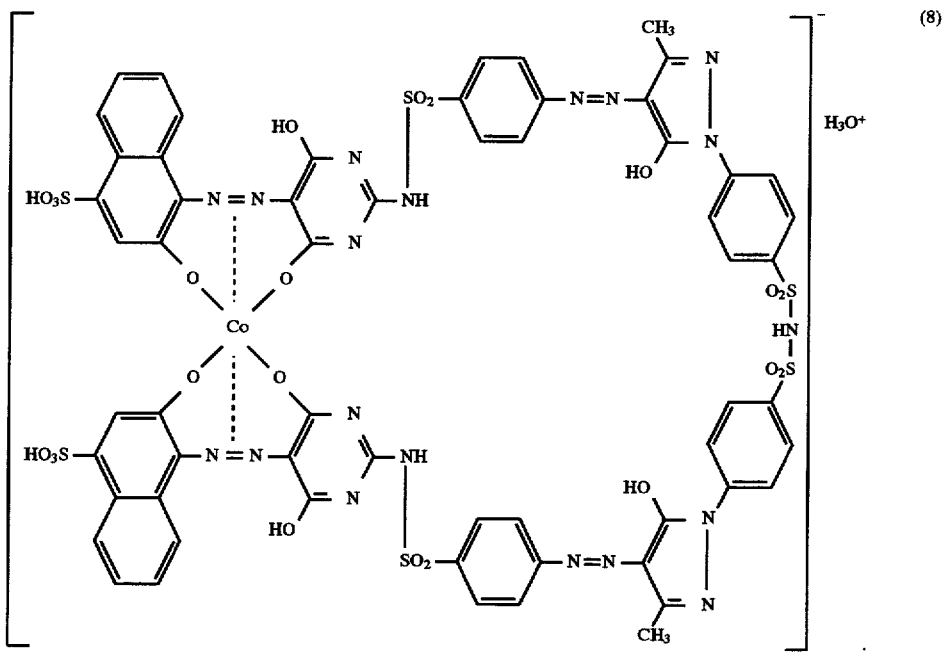

(8)

Example 15bis

The procedure described in Example 15a) and b) is repeated, with the difference that in part b) instead of using

Examples 17 and 17bis

The procedure described in Examples 15 and 15bis is repeated, with the difference that instead of (DK8) there is employed the equivalent amount of (DK10). The obtained cobalt complex (Example 17) dyes leather in orange shades. The obtained chromium complex (Example 17bis) dyes leather in red shades.

Example 18

The procedure described in Example 2 is repeated with the difference that instead of the 24.4 parts of (BK1) there is employed a mixture of 16.3 parts of (BK1) and 5.7 parts of 3-methyl-1-phenyl-5-pyrazolone (=KK1). The obtained dye mixture dyes leather in yellow shades. The dye mixture contains the dye of Example 2 in admixture with a yellow disazo dye that in the form of the free acid corresponds to the formula

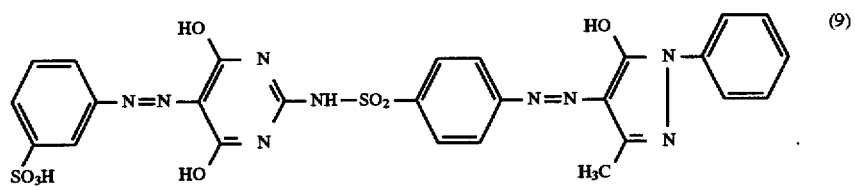
(9)

Example 19

21 parts of (DK 10) are diazotized in conventional way with $NaNO_2$ in the presence of hydrochloric acid and coupled to 23.9 parts of (MK 8), previously dissolved in 50 parts of water and 20 parts of aqueous 25% sodium hydroxide solution. The solution is then heated to 80° C., the pH is adjusted to 5.5 with 10 parts of aqueous 30% hydrochloric acid solution and 20 parts of an aqueous 40% iron trichloride solution are added. When the complexation is completed, the reaction mixture is acidified with 45 parts of aqueous 30% hydrochloric acid solution, cooled to 5° C. with ice and diazotized with 8 parts of sodium nitrite in 25 parts of water. When the bis-diazotization is completed, 24.4 parts of (BK1) dissolved in 50 parts of water and 16 parts of aqueous 25% sodium hydroxide solution are added, and the pH is increased to 9.5 with 40 parts of aqueous 25% sodium hydroxide solution. The dyestuff is finally salted out. It dyes leather in brown shades. It may be represented in the form of the free acid by the following formula

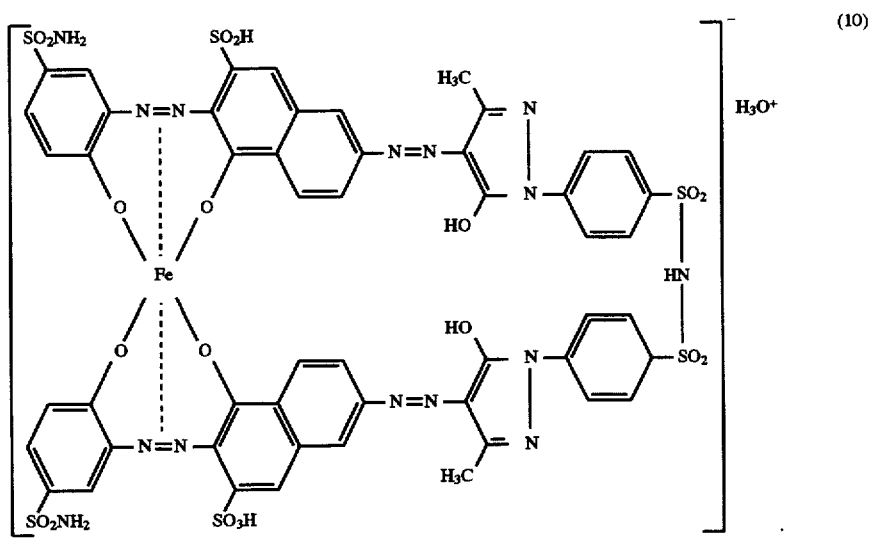
(10)

Examples 20 and 20bis

The procedure described in Examples 17 and 17bis is repeated, with the difference that, instead of (MK(1) there is used the equivalent amount of (MK4). There is obtained in each case a mixture of isomeric metal complexes. The cobaltation product (Example 20) is a dye mixture that dyes leather in red-bordeaux shades. The main components of the mixture may be represented in the free acid form by the following formulae

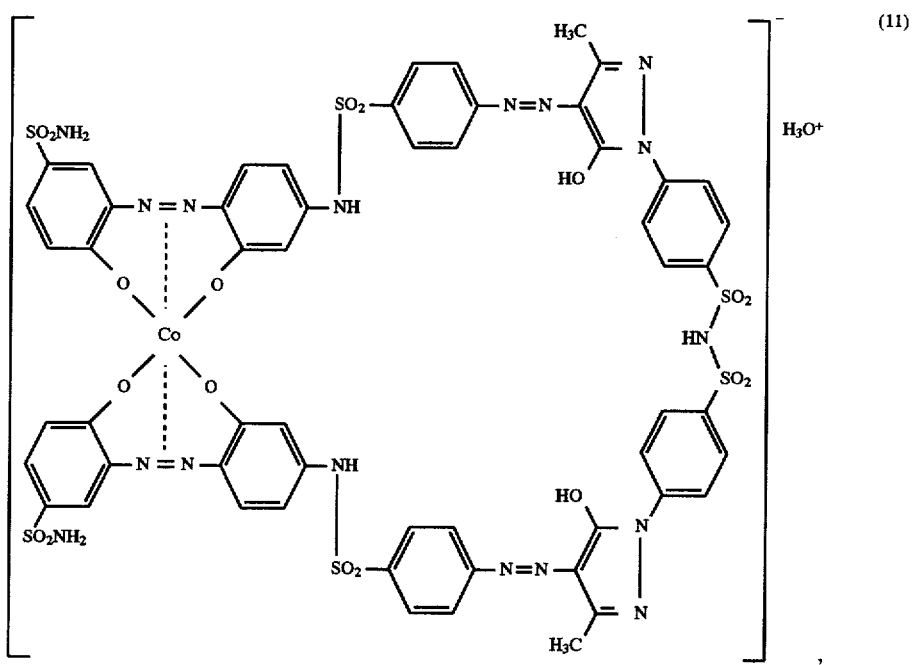 (11)
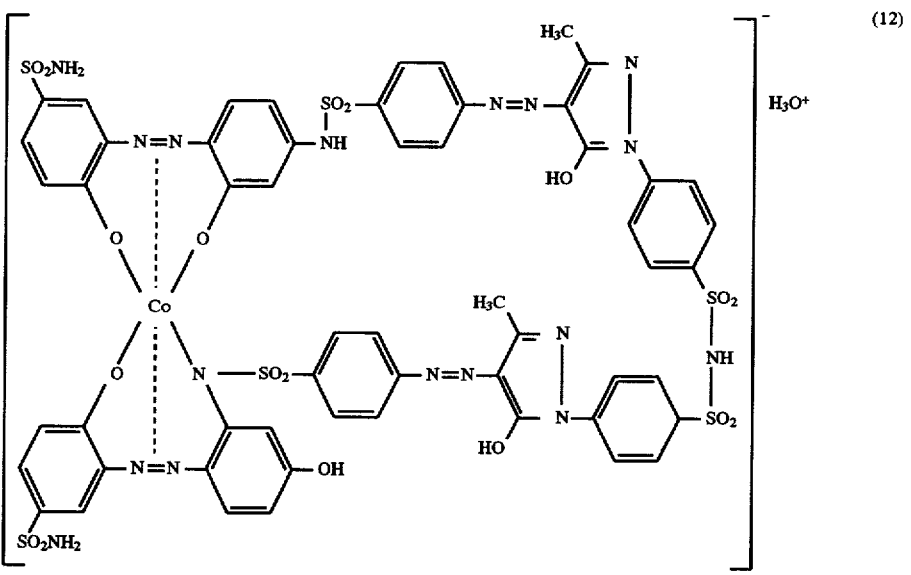 (12)
and

-continued

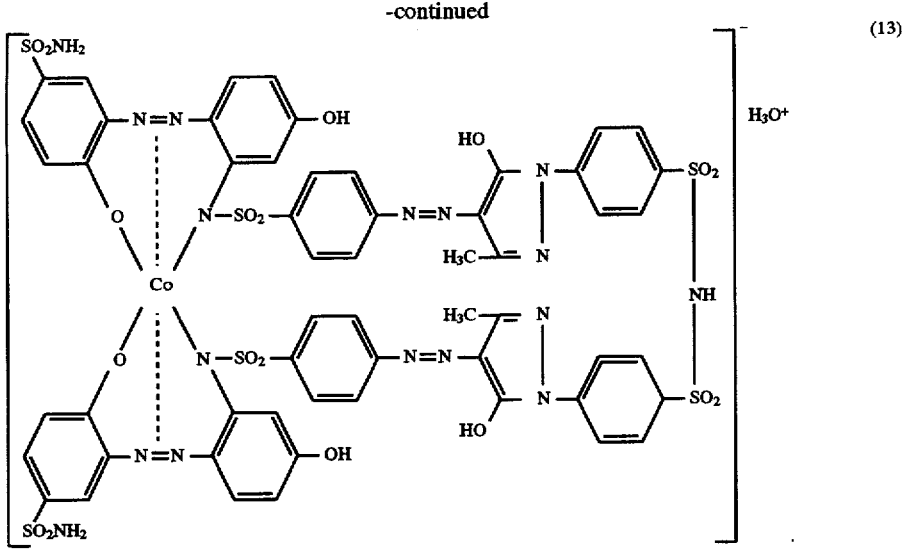

(13)

The dye mixture obtained upon chromation (Example 20bis) dyes leather in bordeaux shades. It has an analogous composition as the cobalt complex mixture of Example 20

Example 21

18.2 parts of (DK2) are diazotized in conventional ray with NaNO$_2$ in the presence of hydrochloric acid and coupled to 28.1 parts of (MK2), which are previously dissolved in 50 parts of rarer and 12 parts of an aqueous 25% sodium hydroxide solution, keeping the pH at 10 by addition of an aqueous 25% sodium hydroxide solution, at a temperature of 10° C. When the coupling reaction is completed the pH is adjusted to 11 by addition of 12 parts of an aqueous 25% sodium hydroxide solution, 24 parts of an aqueous 35% sodium nitrite solution are added and the solution is added dropwise into a mixture of 50 parts of ice and 50 parts of an aqueous 30% hydrochloric acid solution. When the diazotization reaction is completed, a solution of 28 parts of (MK2) in 50 parts of water and 12 parts of an aqueous 25% sodium hydroxide solution is added thereto and the pH is raised to 10 by the addition of 50 parts of an aqueous 25% sodium hydroxide solution. When the coupling reaction is completed, 50 parts of an aqueous 30 1 hydrochloric acid solution are added and the aminodisazodye is diazotized by addition of 24 parts of an aqueous 35% sodium nitrite solution. When the diazotization reaction is completed a solution of 24 parts of (BK1) in 50 parts of water and 25 parts of an aqueous 25% sodium hydroxide solution is added and the pH is raised to 10 by addition of 43 parts of an aqueous 25% sodium hydroxide solution. Finally the pH is adjusted to 5 and the obtained dye is salted out by addition of sodium chloride and suction-filtered. It dyes leather in yellow shades and corresponds in the form of the free acid to the formula

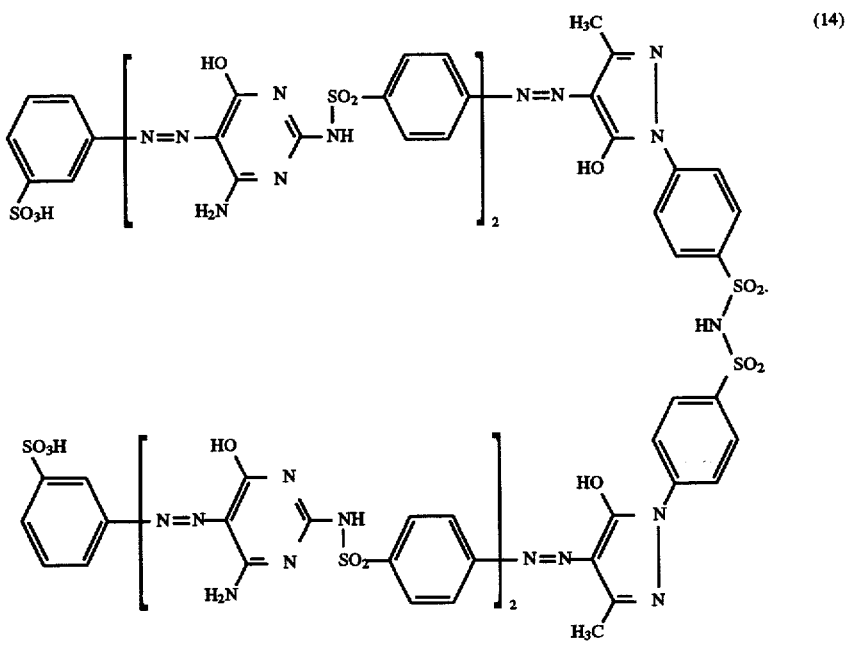

(14)

APPLICATION EXAMPLES

Application Example A 100 parts of a wet blue bovine box side leather are neutralized in a dyeing drum with 250 parts of water and 0.8 parts of sodium bicarbonate at 35° C. during 45 minutes. The leather is then washed with 1000 parts of water at 25° C. After 5 minutes the leather is dyed at 50° C. with 250 parts of water and 0.8 parts of the dye produced according to Example 1, previously dissolved in 80 parts of water of 50° C. After 20 minutes 4 parts of an 80% emulsion of a sulphited fish oil are added for fatting and fatting is continued for 45 minutes. Then the bath is acidified with 0.5 parts of an 85% formic acid solution and drumming is continued for 20 minutes. Finally the liquor is drained off and the leather is rinsed at 25° C. with 1000 parts of water. The leather is drained, dried and cured in conventional way. A leather dyed in a level yellow shade with outstanding fastnesses (in particular wet fastnesses, fastness to dry cleaning, fastness to light and PVC-migration resistance) is obtained.

Application Example B 100 parts of an intermediately dried chrome-tanned suede split leather are wetted back with 800 parts of water at 50° C., 2 parts of 25% ammonia solution and 0.5 parts of the adduct of 10 moles of ethylene oxide to 1 mol of nonylphenol for 90 minutes; the bath is then drained off and 600 parts of water at 50° C., 1 part of a 25% ammonia solution and 1 part of a fat-liquoring agent (an emulsion of fatty acid esters) are added. After 10 minutes, 4 parts of the dye produced according to Example 1, previously dissolved in 400 parts of water of 50° C., are added for pre-dyeing. After 60 minutes, 2 parts of an 85% formic acid are added and drumming is continued for 20 minutes. 2 parts of a 20 X solution of the product obtained by quaternization with dimethylsulphate of the benzylation product of diethylenetriamine are then added and after 20 minutes 2 parts of the same dyestuff as used for pre-dyeing, previously dissolved in 200 parts of water of 50° C., are added. Drumming is continued for 40 minutes, then the bath is acidified with two additions of 1.5 parts of an 85% formic acid solution at an interval of 10 minutes between the two additions. After 10 minutes the bath is drained off and the leather is rinsed, drained, dried and cured as usual. There is obtained a leather dyed in a level yellow shade with outstanding fastnesses (in particular wet fastnesses, fastness to dry cleaning, fastness to light and PVC-migration resistance).

Application Example C 100 parts of chrome-tanned bovine upholstery leather are wetted back with 800 parts of water, 2 parts of a 25% ammonia solution and 3 parts of the adduct of 10 moles of ethylene oxide to 1 mol of nonylphenol at 50° C. during 90 minutes. The bath is then drained off and the leather is treated for 15 minutes with 400 parts of water at 40° C., 1.5 parts of a 25% ammonia solution, 2 parts of a fat-liquoring agent (an emulsion of fatty acid esters) and 1 part of a phenolic syntan (condensation product of phenol and sulphuric acid). 6 parts of the dye obtained in Example 1, previously dissolved in 600 parts of water of 50° C., are added and drumming is continued for 60 minutes. The bath is then acidified with two subsequent additions of 1.5 parts of an 85% formic acid solution, at an interval of 10 minutes. After 10 minutes the leather is rinsed, drained, dried and cured as conventional. There is obtained a leather dyed in a level yellow shade with outstanding fastnesses (in particular wet fastnesses, fastness to dry cleaning, fastness to light and PVC-migration resistance).

Application Example D 100 parts of chrome tanned bovine upholstery leather is wetted back with 800 parts of water, 2 parts of a 25% ammonia solution and 3 parts of the adduct of 10 moles of ethylene oxide to 1 mol of nonylphenol at 50° C. during 90 minutes. The liquor is then drained off and the leather is treated for 15 minutes with 400 parts of water at 40° C., 1.5 parts of a 25% ammonia solution, 2 parts of a fat-liquoring agent (an emulsion of fatty acid esters) and 1 part of a phenolic syntan (condensation product of phenol and sulphuric acid). The leather is then pre-dyed with 4 parts of the dye obtained in Example 1, previously dissolved in 400 parts of water of 50%C. After 60 minutes, the bath is acidified with 1 part of an 85% formic acid solution and, after 10 minutes, 2 parts of a 20% solution of the product obtained by quaternization with dimethylsulphate of the benzylation product of diethylenetriamine are added. The bath is drained off after 20 minutes and the leather is dyed at 50° C. with 400 parts of water and 2 parts of the same dyestuff as used before for pre-dyeing, previously dissolved in 200 parts of water of 50° C., for 40 minutes. The bath is then acidified with 1 part of an 85% formic acid solution and, after 20 minutes, the leather is rinsed, drained, dried and cured as conventional. There is obtained a leather dyed in a level yellow shade with outstanding fastnesses (in particular wet fastnesses, fastness to dry cleaning, fastness to light and PVC-migration resistance).

Application Example E 100 parts of low affinity chrome/vegetable tanned bovine leather is wetted back at 50%C with 1000 parts of water and 0.2 parts of the adduct of 10 moles of ethylene oxide to 1 mole of nonylphenol during 90 minutes. The bath is then drained off and the leather is dyed at 50° C. with 1000 parts of water and 4 parts of the dye obtained in Example 1, previously dissolved in 400 parts of water of 50° C. After 1 hour, the bath is acidified with 2 parts of an 85% formic acid solution, and, after 20 minutes, the leather is rinsed, drained, dried and cured as conventional. There is obtained a leather dyed in a level yellow shade with outstanding fastnesses (in particular wet fastnesses, fastness to dry cleaning, fastness to light and PVC-migration resistance).

Application Example F 100 parts of semichrome sheep leather are wetted back at 45° C. with 1000 parts of water and 0.5 parts of an amphoteric masking agent (a sulpho group containing fatty acid aminoamide) for 1 hour. The leather is pre-dyed with 800 parts of water of 50° C. and 6 parts of the dye obtained in Example 1, previously dissolved in 600 parts of water of 50° C. Drumming is continued until the dye has penetrated inside the leather. The bath is then acidified with 1.5 parts of an 85% formic acid solution and, after 20 minutes, 2 parts of a 20% solution of the product obtained by quaternization with dimethylsulphate of the benzylation product of diethylenetriamine are added. After 20 minutes the leather is dyed with 6 parts of the same dye as used for pre-dyeing, previously dissolved in 600 parts of water of 50°%C. for 40 minutes. The bath is then acidified with 2 parts of an 85% formic acid solution and after 30 minutes the leather is rinsed, drained, dried and cured as conventional. There is obtained a leather dyed in a level yellow shade with outstanding fastnesses (in particular wet fastnesses, fastness to dry cleaning, fastness to light and PVC-migration resistance).

Application Example G 100 parts of chrome tanned crust bovine leather for upholstery are wetted back at 35° C. with 300 parts of water and 0.5 parts of an amphoteric masking agent (a sulpho group containing fatty acid aminoamide) for 20 minutes. The bath is drained off, an the leather is retanned at 35° C. with 150 parts of water, 1 part of a phenolic syntan (65% solution of the condensation product of phenol and sulphuric acid) and 3 parts of a 40% solution of dimethyloldihydroxyethylene urea. After 30 minutes 1.5 parts of sodium formate are added and, after 15 minutes 5 parts of a polypeptide-based retanning agent are added. Drumming is continued for 30 minutes and then the pH of the bath is set to 6 by addition of 1.5 parts of sodium bicarbonate. After 30 minutes the leather is washed for 10 minutes with 300 parts of water at 40° C. Then 150 parts of water at 45° C., 1 part of a fat-liquoring agent (an emulsion of fatty acid esters), 1 part of a 25% ammonia solution and 0.5 parts of a phenolic syntan (condensation product of phenol and sulphuric acid) are added. After 15 minutes the leather is dyed with 3 parts of the dye obtained in Example 1, previously dissolved in 300 parts of water of 50° C., during 90 minutes, i.e. until the dye has fully penetrated. 2 parts of an emulsion of fatty acid esters, 3 parts of a mixture of an esterified synthetic fatty alcohol and a phosphoric acid partial ester of an ethoxylated fatty alcohol and 6 parts of an emulsion of a sulphited fish-oil are added for fat-liquoring and, after 60 minutes, 2 parts of a hydrosoluble melamine-formaldehyde condensate are added for fixation. Drumming is continued for 20 minutes and then the bath is acidified with two additions of 0.75 parts of an 85% formic acid solution diluted with water 1:20 v/v, with an interval of 10 minutes between the two additions. After 10 minutes the leather is rinsed, drained, dried and cured as conventional. There is obtained a leather dyed in a level yellow shade with outstanding fastnesses (in particular wet fastnesses, fastness to dry cleaning, fastness to light and PVC-migration resistance).

Application Example H 100 parts of sheep nappa are washed 40° C. with 200 parts of water and 0.5 parts of an amphoteric masking agent (a sulpho group containing fatty acid aminoamide) for 20 minutes. The bath is drained off, 200 parts of water at 35°%C and 1.2 parts of sodium formate are added and drumming is continued for 15 minutes. 4 parts of a polypeptide-based retanning agent are then added and after 30 minutes 0.6 parts of sodium carbonate are added to adjust the pH of the bath to 5.8–6.0. After 40 minutes 4 parts of polyacrylic-acid-based retanning agent are added and drumming is continued for 30 minutes; 2 parts of a water-soluble urea/formaldehyde condensate are then added and after 30 minutes the bath is drained off. Then 150 parts of water at 40° C., 1 part of a 25% ammonia solution and 2 parts of a fat-liquoring agent (an emulsion of fatty acid esters) are added. After 10 minutes the leather is dyed with 3 parts of the dye obtained in Example 1, previously dissolved in 300 parts of water of 50° C., during 90 minutes. 2 parts of an emulsion of fatty acid esters, 6 parts of an emulsion of a sulphited fish-oil and 3 parts of an aqueous emulsion of fatty alcohol phosphoric acid partial esters are added for fat-liquoring. Drumming is continued for 60 minutes and then the bath is acidified with 1.5 parts of an 85% formic acid solution. After 30 minutes the bath is drained off and the leather is rinsed, drained, dried and cured as conventional. There is obtained a leather dyed in a level yellow shade with outstanding fastnesses (in particular wet fastnesses, fastness to dry cleaning, fastness to light and PVC-migration resistance).

Application Example I

Application Example B is repeated, with the difference that after fat-liquoring and before the conclusive formic acid addition the bath is drained off, 200 parts of water at 50° C. and 2 parts of a hydrosoluble polymeric reaction product of epichlorohydrin and dimethylamine are added, drumming is continued for 30 minutes, thereafter 0.5 parts of 2—fatty alkyl imidazoline are added and drumming is continued for further 20 minutes. The bath is then drained off and the leather is rinsed, drained, dried and cured as conventional. There is obtained a leather dyed in a level yellow shade with outstanding fastnesses (in particular wet fastnesses, fastness to dry cleaning, fastness to light and PVC-migration resistance).

Analogously as the yellow dye according to Example 1, the dyes of each of Examples Ibis to 21 are used in each of the above Application Examples A to I, by which there are also obtained dyeings of corresponding shades, depths and fastnesses.

The following Table contains further Application Examples (Ap. Ex. J to U) in which Application Examples C, D or G (as indicated) are repeated, with the difference that in place of the yellow dye of Example 1 there is employed the same amount of a dye mixture of the red 1:2 chromium complex dye of Example 17bis, which in the following table is indicated as "Red Ex. 17bis", and another dye which is the dye of Example 2 or 21, indicated in the following table as "Yellow Ex. 2" or "Yellow Ex. 21" respectively, or a Colour Index Acid Dye identified by its "Colour Index" denomination, the two dyes of the mixture being employed in the weight ratio of 2 parts of Dye 1 to 1 part of Dye 2.

TABLE

| Ap. Ex. | Dye 1 | Dye 2 | dyeing as in Ap. Ex. | shade on leather |
|---|---|---|---|---|
| J | Red Ex. 17bis | Yellow Ex. 2 | C | orange |
| J' | Red Ex. 17bis | Yellow Ex. 21 | C | orange |
| K | Yellow Ex. 2 | Red Ex. 17bis | C | yellowish orange |
| K' | Yellow Ex. 21 | Red Ex. 17bis | C | yellowish orange |
| L | Red Ex. 17bis | C.I. Acid Black 233 | C | reddish brown |
| M | C.I. Acid Black 233 | Red Ex. 17bis | C | reddish dark brown |
| N | Red Ex. 17bis | Yellow Ex. 2 | D | orange |
| N' | Red Ex. 17bis | Yellow Ex. 21 | D | orange |
| O | Yellow Ex. 2 | Red Ex. 17bis | D | yellowish orange |
| O' | Yellow Ex. 21 | Red Ex. 17bis | D | yellowish orange |
| P | Red Ex. 17bis | C.I. Acid Black 233 | D | reddish brown |
| Q | C.I. Acid Black 233 | Red Ex. 17bis | D | reddish dark brown |
| R | Red Ex. 17bis | Yellow Ex. 2 | G | orange |
| R' | Red Ex. 17bis | Yellow Ex. 21 | G | orange |
| S | Yellow Ex. 2 | Red Ex. 17bis | G | yellowish orange |
| S' | Yellow Ex. 21 | Red Ex. 17bis | G | yellowish orange |
| T | Red Ex. 17bis | C.I. Acid Brown 432 | G | brownish red |
| U | C.I. Acid Brown 432 | Red Ex. 17bis | G | reddish brown |

We claim:
1. A polyazo dye of the formula

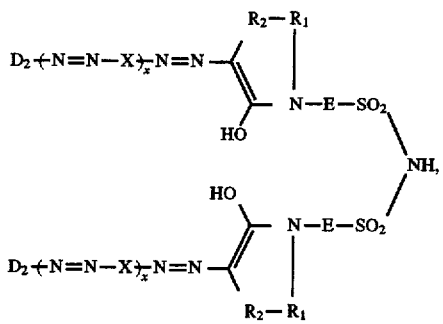

(IVa)

wherein

E is phenylene, substituted or unsubstituted with $C_{1-4}$-alkyl, $C_{1-4}$-alkoxy, or chloro; or naphthylene;

the group $-R_1-R_2-$ is $-CH_2-$, $-CH_2-CH_2-CH_2-$, or $-CH_2-CH(CH_3)-$;

each

X is the radical of a compound of the formula H—X—$NH_2$ which will undergo a coupling reaction with a diazo compound and which is capable of being diazotized;

each $_x$ independently is 1 or 2; and each $D_2$ is independently the radical of a diazo component of the formula $DNH_2$; which is selected from the group consisting of:

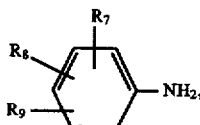

(a₁)

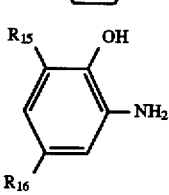

(a₂)

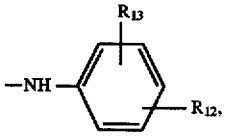

(a₃)

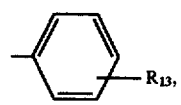

(a₄)

and

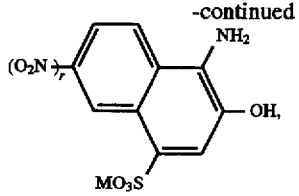

(a₅)

wherein $R_7$ signifies hydrogen, nitril, trifluoromethyl, nitro, $-SO_3M$, $-SO_2NR_{10}R_{11}$, $-COOM$ or $-CONR_{10}R_{11}$, $R_8$ signifies hydrogen, nitro, $-SO_3M$, $-SO_2NR_{10}$, $R_{11}$, trifluoromethyl, nitril, $-COOM$, $-CONR_{10}R_{11}$, $C_{1-4}$-alkyl, $C_{1-4}$-alkoxy, halogen or $C_{1-2}$-mercapto-alkyl, $R_9$ signifies hydrogen, $C_{1-4}$-alkyl, $C_{1-4}$-alkoxy, halogen, $C_{1-2}$-mercapto-alkyl, $-NH-Ac'$, $-NH-CO-O-CH_3$ or a radical of formula

(c₁)

$R_{10}$ signifies hydrogen, $C_{1-4}$-alkyl, $C_{1-3}$-alkylene-R' or $C_{2-3}$-hydroxyalkyl, $R_{11}$ signifies hydrogen, $C_{1-4}$-alkyl, $C_{1-3}$-alkylene-R', $C_{2-3}$—hydroxyalkyl, benzyl or a radical of formula

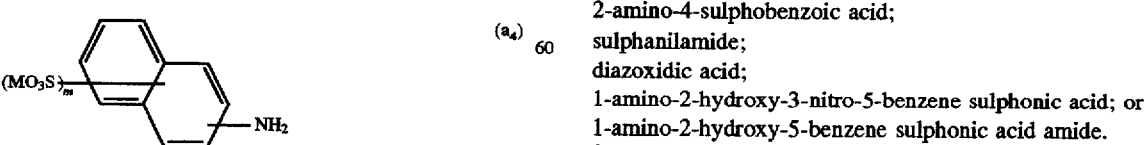

(c₂)

$R_{12}$ signifies hydrogen, nitro or $-SO_3M$, $R_{13}$ signifies hydrogen, methyl, chlorine, nitro, $-COOM$ or $-SO_3M$, $R_{14}$ signifies nitril, carbamoyl or $-COOM$, $R_{15}$ signifies hydrogen, halogen, nitro, $-SO_3M$, $-SO_2NR_{10}R_{11}$, methylsulphonyl, $C_{1-4}$-alkyl or $-NH-Ac'$, $R_{16}$ signifies hydrogen, halogen, nitro, $-SO_3M$, $-SO_2NR_{10}R_{11}$, methylsulphonyl, $C_{1-4}$-alkyl or $-NH-Ac'$, $R_{17}$ signifies nitro, $-SO_3M$ or $SO_2NR_{10}R_{11}$, m signifies 0 or 1 and signifies 0 or 1.

2. The polyazo dye of claim 1 in which the $DNH_2$ is selected from the group consisting of:
anthranilic acid;
metanilic acid;
orthanilic acid;
sulphanilic acid;
2-amino-5-sulphobenzoic acid;
2-amino-4-sulphobenzoic acid;
sulphanilamide;
diazoxidic acid;
1-amino-2-hydroxy-3-nitro-5-benzene sulphonic acid; or
1-amino-2-hydroxy-5-benzene sulphonic acid amide.

3. The polyazo dye of claim 1 in which
H—X—$NH_2$ is a compound of formula

HO—Y—$E_1$—$NH_2(m_3)$ wherein —E₁— is phenylene, substituted or unsubstituted with $C_{1-4}$-alkyl, $C_{1-4}$-alkoxy, or chloro; or naphthylene;

—G— is hydroxybenzyl; 5-pyrazolonyl; or -aminopyrazoyl; amino- or hydroxy-pyrimidyl; and —Y— is a heteroatomic bridge or, if —G— is of the 5-pyrazolonyl or -aminopyrazoyl, the direct bond linked to the 1-position of the pyrazoyl or pyrazolonyl;

or

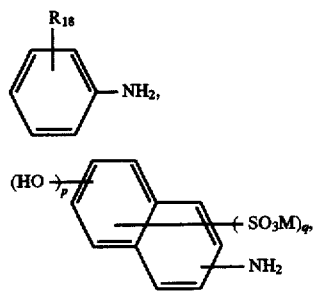

(m1)

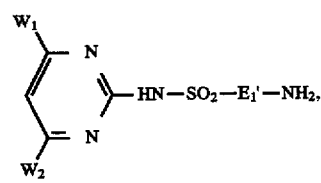

(m2)

wherein $R_{18}$ signifies hydrogen, $C_{1-4}$-alkyl, $C_{1-4}$-alkoxy, hydroxy, —NH₂ or —NH—Ac', Ac' signifies an aliphatic acyl group, p signifies 0 or 1 and q signifies 0, 1 or 2.

4. The polyazo dye of claim 3 in which the compound of formula (m₃) is selected from the group consisting of:

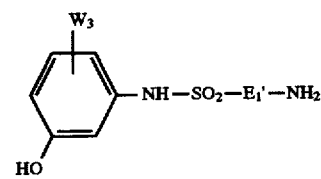

(VIa)

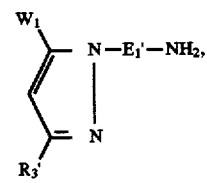

(VIb)

(VIc)

in which $W_1$ signifies, primary amino group or hydroxy, $W_2$ signifies a primary amino group or hydroxy, $W_3$ signifies hydrogen, hydroxy, a primary amino group, $C_{1-4}$-alkyl or halogen $R_3$ is $C_{1-4}$-alkyl or carboxy.

5. The polyazo dye of claim 4 in which

—E— is phenylene-1, 4 and $W_3$ is hydrogen.

6. The polyazo dye of claim 1 in which the compound H—X—NH₂ is selected from the group consisting of:

2-sulphanilylamino-3H-pyrimidine-4,6—dione;

6-amino-2-sulphanilylamino-3H-pyrimidine-4-one;

4,6-diamino-2-sulphanilylamino-pyrimidine;

4-amino-N-(3'-hydroxyphenyl)-benzenesulphonamide;

1-(4'-aminophenyl)-3-methyl-5-aminopyrazole;

1-(3'-aminophenyl)-3-methyl-5-pyrazolone; or 6-amino-1-naphthol-3-sulphonic acid.

7. A polyazo dye of the formula

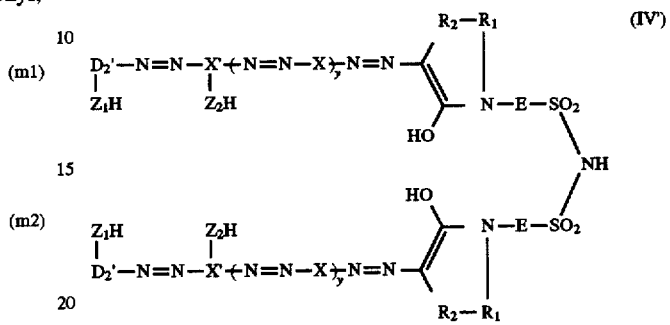

(IV')

wherein

E is phenylene, substituted or unsubstituted with $C_{1-4}$-alkyl, $C_{1-4}$-alkoxy, or chloro; or naphthylene;

the group

—R₁—R₂— is —CH₂—, CH₂—C—H₂—CH₂—, or —CH₂—CH(CH₃)—;

each

X or X' is independently the bivalent aromatic radical of 1–4 aromatic rings;

each y is independently 0 or 1; and each $D_2'$ is the ortho-bivalent radical;

$Z_1H$ is —OH or —COOH and is in ortho-position to the diazotizable amino group;

and $Z_2H$ is —OH or —NH₂, and in ortho-position to the D₂—N=N-moiety.

8. A metal complex of at least one metallizable azo dye according to claim 7, or a mixture of such complexes.

9. A metal complex according to claim 8 in which the metal is chromium, cobalt, iron, copper, nickel manganese, titanium, zirconium, or aluminum.

10. A dye mixture comprising at least one dye (AZ) as defined below and at least one dye (BZ) of the formula

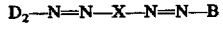

D₂—N=N—X—N=N—B         (XIII), in which B is the radical of a coupling component HB as defined below;

in which the dye (AZ) is of formula (Iva) or (IVb):

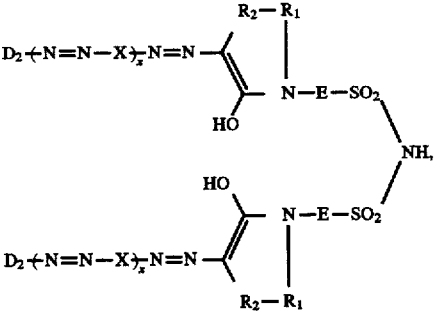

(IVa)

wherein the substituents in the formula (IVa) are as defined in claim 1;

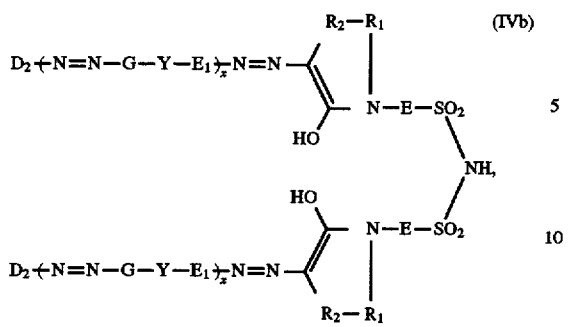

(IVb)

wherein the substituents in the formula (IVb) are as defined in claim 3.

11. The dye mixture according to claim 10 of a polyazo dye of formula (IV')

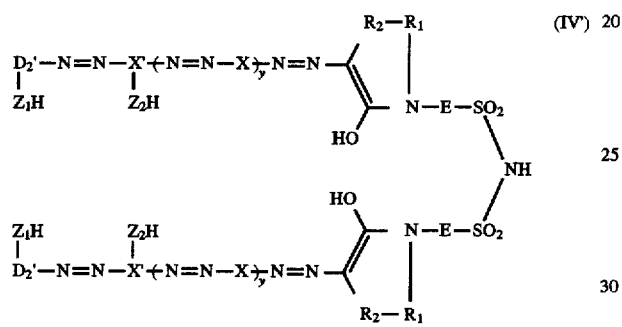

(IV')

wherein

E is phenylene, substituted or unsubstituted with $C_{1-4}$-alkyl, $C_{1-4}$-alkoxy, or chloro; or naphthylene;

the group

—$R_1$—$R_2$— is —$CH_2$—, —$CH_2$—$CH_2$—$CH_2$—, or —$CH_2$—$CH(CH_{13})$—;

each

X or X' is independently the bivalent aromatic radical of 1–4 aromatic rings;

each is independently 0 or 1; and each $D_2'$ is the ortho-bivalent and radical;

$Z_1H$ is —OH or —COOH and is in ortho-position to the diazotizable amino group;

and $Z_2H$ all is —OH or —$NH_2$, and in ortho-position to the $D'_2$—N=N-moiety;

and an azo dye of formula

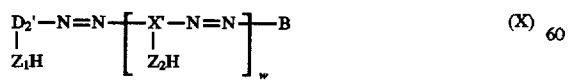

(X)

wherein w is 0, 1 or 2, and

B is the radical of a coupling component H—B which is selected from the group consisting of:

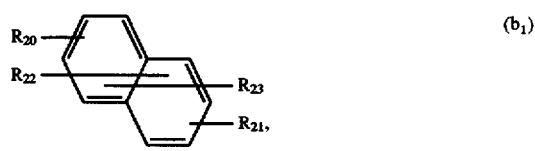

(b₁)

(b₂)

(b₃)

(b₄)

(b₅)

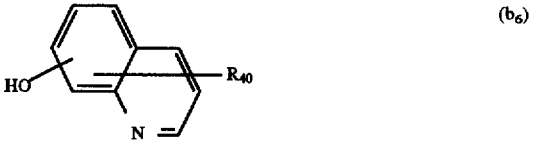

(b₆)

and

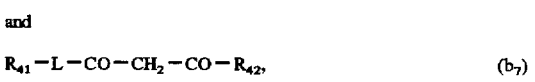

$R_{41}-L-CO-CH_2-CO-R_{42}$,  (b₇)

wherein $R_{20}$ signifies hydrogen, —$OR_{24}$ or —$NHR_{24}$, $R_{21}$ signifies hydrogen, —$OR_{24}$ or —$NHR_{24}$, at least one of $R_{20}$ and $R_{21}$ having a significance other than hydrogen, $R_{22}$ signifies hydrogen, —$SO_3M$, —$SO_2NR_{10}R_{11}$, —COOM or —$CONR_{10}R_{11}$, $R_{23}$ signifies hydrogen, —$SO_3M$, —$SO_2NR_{10}R_{11}$, —COOM or —$CONR_{10}R_{11}$, $R_{24}$ signifies hydrogen, $C_{1-4}$-alkyl, Ac" or a radical of formula

(c₃)

Ac" signifies the acyl radical of an aliphatic carboxylic acid,

—Q— signifies —CO— or —$SO_2$—, $R_{25}$ signifies hydrogen, methyl, —NH—Ac', —COOM or —OH or —$NO_2$, $R_{26}$ signifies —OH or —$NH_2$, $R_{27}$ signifies hydrogen, $C_{1-4}$-alkyl, $C_{1-4}$alkoxy, —OH, —$NR_{29}R_{30}$ or —NH—Ac', $R_{28}$ signifies hydrogen, $C_{1-4}$-alkyl or $C_{1-4}$-alkoxy, $R_{29}$ and $R_{30}$, independently, signify hydrogen, $C_{1-2}$-alkyl or $C_{2-3}$-hydroxy-alkyl, $R_{31}$ signifies hydrogen, sulphonaphthyl or a radical of formula

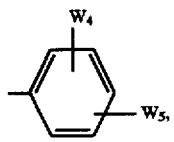 (c₄)

$W_4$ hydrogen, halogen, methyl, methoxy or —COOM, $W_5$ signifies hydrogen, halogen, trifluoromethyl, nitril, nitro, —COOM, —SO₃M or —SO₂NR₁₀R₁₁, $R_{32}$ signifies $C_{1-4}$-alkyl, phenyl, —COOM, —CONR₁₀R₁₁, —COOCH₃ or —COOC₂H₅, $R_{33}$ signifies =O or =NH, $R_{34}$ signifies hydrogen, unsubstituted amino, phenylamino, sulphonaphthyl, open-chain $C_{1-8}$-alkyl, $C_{6-9}$-cycloalkyl, carboxy-($C_{1-4}$-alkyl, $C_{2-4}$-alkyl substituted with hydroxy, methoxy, ethoxy or a sulpho group in one of the positions β to ω, or a radical of formula (c₄), $R_{35}$ hydrogen, nitril, acetyl, —COOM, carbamoyl, —SO₃M, pyridinio or 2-methylpyridinio, $R_{36}$ hydrogen, hydroxy, methyl, carboxy, phenyl, sulphomethyl or carbamoyl, $R_{37}$ hydroxy, primary amino, nitrilamino, thiol or a radical of formula

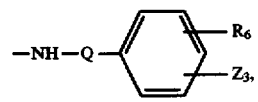 (c₅)

$R_{38}$ signifies hydroxy or primary amino, $R_{39}$ signifies hydroxy or primary amino, $R_{40}$ signifies hydrogen, methyl, chlorine, chloromethyl or chloroacetyl, —L— signifies —O—, —NH— or the direct bond, $R_{41}$ signifies naphthyl, sulphonaphthyl or disulphonaphthyl or a radical of formula (c₄), $R_{42}$ signifies $C_{1-4}$-alkyl, $Z_3$ signifies —NH₂, —NHAc' or —NO₂ and, where in formula (b₄) $R_{35}$ stands for pyridinio or orthomethylpyridinio, an acid group present in the may molecule be in the form of the respective anion (e.g. a sulpho group in the form of —SO₃) to form the counterion in the form of the inner salt.

12. A polyazo dye of claim 7 in which $D_2^1$ is a diazo component.

13. The polyazo dye of claim 7 in which the diazo component of formula HZ₁—$D_2^1$—NH₂ is selected from the group consisting of:

anthranilic acid;
methanilic; acid;
orthanilic acid;
sulphanilic acid;
2-amino-5-sulphobenzoic acid;
2-amino-4-sulphobenzoic acid;
sulphonilamide;
diazoxidic acid;
1-amino-2-hydroxy-3-nitro-5-benzene sulphonic acid; or
1-amino-2-hydroxy-5-benzenesulphonic acid amide.

14. The polyazo dye of claim 7 in which the compound of formula H—X¹(Z₂H)—NH₂ or H—X—NH₂ is selected from the group consisting of:

2-sulphanilylamino-3H-pyrimidine-4,6-dione;
6-amino-2-sulphanilylamino-3H-pyrimidine-4-one
4,6-diamino-2-sulphanilylamino-pyrimidine;
4-amino-N-(3'-hydroxyphenyl)-benzene sulphonamide,
1-(4'-aminophenyl)-3-methyl-5-aminopyrazole;
1-(3'-aminophenyl)-3-methyl-5-pyrazolone; or
6-amino-1-naphthol-3-sulphonic acid.

\* \* \* \* \*